(12) United States Patent
Didzbalis et al.

(10) Patent No.: US 11,858,955 B2
(45) Date of Patent: *Jan. 2, 2024

(54) FLAVOR COMPOSITION CONTAINING HMG GLUCOSIDES

(71) Applicant: MARS, INCORPORATED, McLean, VA (US)

(72) Inventors: John Didzbalis, Cranford, NJ (US); John P. Munafo, Hackettstown, NJ (US)

(73) Assignee: MARS, INCORPORATED, McLean, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/929,298

(22) Filed: Sep. 1, 2022

(65) Prior Publication Data

US 2023/0086494 A1    Mar. 23, 2023

Related U.S. Application Data

(60) Continuation of application No. 16/542,665, filed on Aug. 16, 2019, now abandoned, which is a division of application No. 14/772,682, filed as application No. PCT/US2014/023727 on Mar. 11, 2014, now Pat. No. 10,414,787.

(60) Provisional application No. 61/785,702, filed on Mar. 14, 2013.

(51) Int. Cl.
| | | |
|---|---|---|
| *C07H 17/04* | (2006.01) | |
| *A23L 27/20* | (2016.01) | |
| *A23G 4/06* | (2006.01) | |
| *C07H 15/04* | (2006.01) | |
| *A23L 27/00* | (2016.01) | |

(52) U.S. Cl.
CPC .............. *C07H 17/04* (2013.01); *A23G 4/06* (2013.01); *A23L 27/2052* (2016.08); *A23L 27/88* (2016.08); *C07H 15/04* (2013.01)

(58) Field of Classification Search
CPC ......... C07H 17/04; C07H 15/04; A23L 27/88; A23L 27/2052
See application file for complete search history.

(56) References Cited

U.S. PATENT DOCUMENTS

| | | | |
|---|---|---|---|
| 2,107,133 A | 2/1938 | Snelling | |
| 2,500,919 A | 3/1950 | Cahn | |
| 3,716,379 A | 2/1973 | Van | |
| 3,852,479 A | 12/1974 | Yokotsuka et al. | |
| 3,912,822 A | 10/1975 | Yokotsuka et al. | |
| 5,087,460 A * | 2/1992 | Cherukuri ............. | A23G 4/066 426/5 |
| 6,251,443 B1 | 6/2001 | Chigurupati et al. | |
| 10,414,787 B2 * | 9/2019 | Didzbalis ............... | C07H 15/04 |

FOREIGN PATENT DOCUMENTS

| | | |
|---|---|---|
| EP | 1361799 B1 | 4/2006 |
| EP | 1856988 A1 | 11/2007 |
| EP | 1856988 B1 | 9/2017 |
| EP | 2983508 B1 | 5/2018 |
| WO | 2014159452 A1 | 10/2014 |

OTHER PUBLICATIONS

Burkard Wald et al., Quercetin 3-O-[6"-(3-hydroxy-3-methylglutaroyl)-[beta]-galactoside] from blackberries, Quercetin 3-O-[6"-(3-hydroxy-3-methylglutaroyl)-[beta]-galactoside] from blackberries, Mar. 1986, n/a, 25, Phytochemistry.
Carnat et al., The aromatic and polyphenolic composition of Roman camomile tea, Fitoterapia, 2004, pp. 32-38, 75.
Cho Mi Jin et al, Flavonol glycosides and antioxidant capacity of various vlackberr and blueberry genotyes determined by high-performance liquid chromatography mass spectrometry, Flavonol glycosides, Jun. 20, 2005, 1-10, vol. 85 issue 13, Journal of the Science of Food and Agriculture.
Kim, S. H. et al., Inhibition of antigen-induced degranulation by aryl compounds isolated from the bark of Betula platyphylla in RBL-2H cells, Inhibition of antigen-induced degranulation by aryl compounds isolated from the bark of Betula platyphylla in RBL-2H cells, Mar. 2009, 2824-2827, 20, n/a.
Kunnika et al., Influence of enzyme treatment on bioactive compounds and colour stability of betacyanin in flesh and peel of red dragon fruit *Hylocereus polyrhizus* (Weber) Britton and Rose, International Food Research Journal, 2011, pp. 1437-1448, 18(4).
Yoshiteru Ida et al., Five4 Monoterpene Glycosides from Zingiberis Rhizome, Five4 Monoterpene Glycosides from Zingiberis Rhizome, Jan. 1, 2005, 1-12, 65.

* cited by examiner

*Primary Examiner* — Nikki H. Dees

(57) ABSTRACT

A flavor composition containing at least one HMG glucoside compound that can be used to enhance the taste of edible compositions including sweet goods, such as confectionery goods, and savory goods, such as pet foods.

15 Claims, 2 Drawing Sheets

FLAVOR COMPOSITION CONTAINING HMG GLUCOSIDES

CROSS-REFERENCE TO RELATED APPLICATION

The present application is a continuation of U.S. patent application Ser. No. 16/542,665, filed on Aug. 16, 2019, which is a divisional of U.S. patent application Ser. No. 14/772,682, filed on Sep. 3, 2015, now U.S. Pat. No. 10,414,787, which is a U.S. National Stage Patent Application under 35 U.S.C. § 371 of International Application No. PCT/US2014/023727, filed on Mar. 11, 2014, which claims priority to U.S. Provisional Application Serial No. 61/785,702, filed on Mar. 14, 2013, the contents of each of which is are incorporated by reference in its their entirety herein.

FIELD

The present application relates to HMG glucosides and flavor compositions that include at least one HMG glucoside compound. The flavor compositions can be used to enhance or modify the taste and/or flavor of various edible compositions such as sweet goods and savory goods. The flavor compositions can include combinations of compounds, and can be added to edible compositions in various delivery system formats.

BACKGROUND

Taste profiles for edible compositions include basic tastes such as sweet, salt, bitter, sour, umami and kokumi. Chemical compounds that elicit these tastes are often referred to as tastants. It is hypothesized that tastants are sensed by taste receptors in the mouth and throat which transmit signals to the brain where the tastants and resulting taste profiles are registered. In addition to taste profiles, edible compositions are also known to have flavor profiles. Chemical compounds that contribute to flavor profiles can be aromatic compounds that are often referred to as flavorants. It is hypothesized that flavorants are sensed by receptors in the mouth, nose, and throat. Taken together, the taste and flavor profiles resulting from the various tastants and flavorants contribute to the sensory experience users have when consuming the edible compositions. The sensory experience can also include various texture and temperature/thermal aspects.

While there have been recent advances in taste and flavor technologies, there remains a need for compounds that can enhance or modify the sensory experience of edible compositions by enhancing or modifying the taste, texture, and/or flavor profiles of edible compositions. The enhancement or modification can be to increase the intensity of a desirable attribute, to replace a desirable attribute that is not present or somehow lost in the edible composition, or to decrease the intensity of an undesirable attribute. It is further desirable to be able to use tastants to enhance or modify the texture of an edible composition.

Vegetable proteins, such as wheat and soy, can be hydrolyzed to produce hydrolysates that can be used as flavor enhancers (i.e. soy sauce). In EP1312268A1 to Nestle, wheat protein forms the starting material that is hydrolyzed to form pyroglutamic acid tripeptides that provide umami taste. Umami taste is known to produce organoleptic affects including providing mouthfeel and roundness. Umami taste effect is usually described in comparison to the taste provided by monosodium glutamate (MSG). Taking a purely synthetic approach to umami compounds, U.S. Pat. No. 5,780,090 to Firmenich describes tripeptides with a hydrophobic amino acid residue and at least one acidic amino acid residue. These tripeptides provide fuller, richer texture (i.e. an umami effect). However, neither of these publications describe compounds that can modify other taste, flavor and/or texture sensations. Thus, there remains a need for a flavor modifier that can modify other taste, flavor and/or texture sensations.

SUMMARY OF THE INVENTION

The present application is directed to flavor compositions and methods for making and modifying such compositions across a variety of food compositions. Specifically, the present application is directed to compositions comprising one or more 3-hydroxy-3-methylglutaric acid (HMG) glucosides.

In certain embodiments, the flavor compositions of the present application comprise an HMG glucoside comprising the following structure, Formula I.

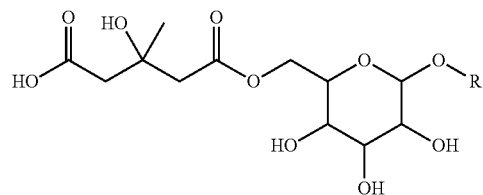

wherein R is described herein below. The present application also provides salts and esters of the compounds of Formula I.

In certain embodiments, the compounds of the application comprise the following structure (Formula II):

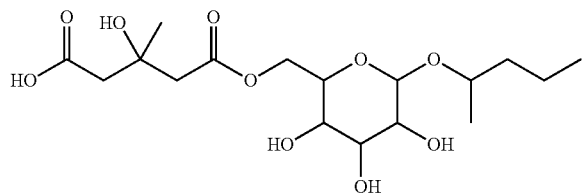 [SMILES: CCCC(C)OC1OC(COC(=O)CC(C)(O)CC(=O)O)C(O)C(O)C1O]

In certain embodiments, the compounds of the application comprise the following structure (Formula III):

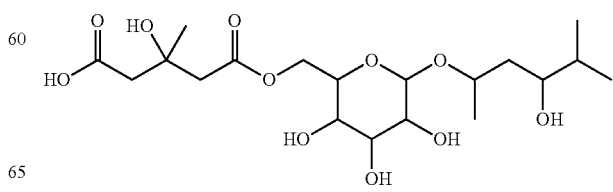

In certain embodiments, the compounds of the application comprise the following structure (Formula IV):

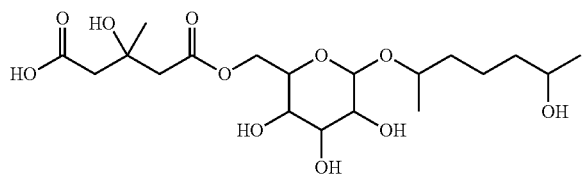 [SMILES: CC(O)CCCC(C)OC1OC(COC(=O)CC(C)(O)CC(=O)O)C(O)C(O)C1O]

In certain embodiments, the compounds of the application comprise the following structure (Formula V):

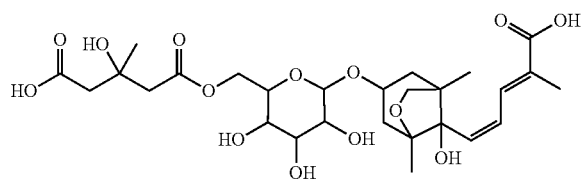 [SMILES: C/C(=C\C=C/C1(O)C2(C)COC1(C)CC(OC1OC(COC(=O)CC(C)(O)CC(=O)O)C(O)C(O)C1O)C2)C(=O)O]

In certain embodiments, the compounds of the application comprise stereoisomers of Formula I.

In certain embodiments, the present application provides methods of modifying the taste and/or flavor and/or texture of a food product, which comprise providing a flavor composition, for example, an HMG glucoside compound such as, but not limited to, an HMG glucoside of Formula I, or combinations thereof, and admixing the flavor composition with a food product.

In certain embodiments of the present application, the flavor composition is admixed with a food product in an amount effective to provide a mouth watering and/or lubricating and/or slippery mouthfeel. In certain embodiments, the flavor composition is admixed with a food product in an amount effective to increase or decrease a mouth watering and/or lubricating and/or slippery mouthfeel present in the food product.

In certain embodiments of the present application, the flavor composition is admixed with a food product in an amount effective to provide an astringent mouthfeel. In certain embodiments, the flavor composition is admixed with a food product in an amount effective to increase or decrease an astringent mouthfeel present in the food product.

In certain embodiments, the flavor composition is admixed with a food product at a concentration of from about 0.1 to about 5000 ppm (parts-per-million). In certain embodiments, the flavor composition is admixed with a food product at a concentration of from about 0.1 to about 500 ppm. In certain embodiments, the flavor composition is admixed with a food product at a concentration of from about 0.1 to about 100 ppm. In certain embodiments, the flavor composition is admixed with a food product at a concentration of from about 0.1 to about 50 ppm.

In certain embodiments, the flavor composition is admixed with a food product at a concentration of about 100 ppm.

In certain embodiments, the flavor composition is admixed with a food product at a concentration of from about 0.1 to about 100 ppb (parts-per-billion). In certain embodiments, the flavor composition is admixed with a food product at a concentration of from about 0.1 to about 50 ppb. In certain embodiments, the flavor composition is admixed with a food product at a concentration of from about 0.1 to about 10 ppb.

In certain embodiments, the flavor composition is admixed with a food product at a concentration of from about 0.0001 to about 99.9% weight/weight (w/w). In certain embodiments, the flavor composition is admixed with a food product at a concentration of from about 0.0001 to about 1.0% w/w. In certain embodiments, the flavor composition is admixed with a food product at a concentration of from about 0.0001 to about 0.5% w/w.

In certain embodiments of the present application, the flavor composition is admixed with a food product in an amount effective to modulate, enhance or decrease the taste profile of an edible composition.

In certain embodiments of the present application, the flavor composition is admixed with a food product in an amount effective to modulate, enhance or decrease the flavor profile of an edible composition.

In certain embodiments of the present application, the flavor composition is admixed with a food product in an amount effective to modulate, enhance or decrease the texture profile of an edible composition.

In certain embodiments, the present application provides methods of preparing a flavor composition. In certain embodiments, the methods comprise hydrolyzing a food product source, for example, cacao, wheat or soy, to produce a hydrolysate comprising the flavor composition. In certain embodiments, the hydrolysate is admixed with a food product.

In certain embodiments the flavor compositions of the present application are prepared from a food product source that is fractionated and/or extracted to form an enriched HMG glucoside composition comprising the HMG glucosides of the present application.

In certain embodiments the flavor compositions of the present application are prepared from a food product source that is hydrolyzed and fractionated and/or extracted to form an enriched HMG glucoside composition comprising the HMG glucosides of the present application.

In certain embodiments, the methods of preparing a flavor composition comprises synthesizing an HMG glucoside flavor composition such as, but not limited to, an HMG glucoside of Formula I, or combinations thereof. In certain embodiments, the synthesis methods are synthetic synthesis methods.

The foregoing has outlined rather broadly the features and technical advantages of the present application in order that the detailed description that follows may be better understood. Additional features and advantages of the application will be described hereinafter which form the subject of the claims of the application. It should be appreciated by those skilled in the art that the conception and specific embodiment disclosed may be readily utilized as a basis for modifying or designing other structures for carrying out the same purposes of the present application. It should also be realized by those skilled in the art that such equivalent constructions do not depart from the spirit and scope of the application as set forth in the appended claims. The novel features which are believed to be characteristic of the application, both as to its organization and method of operation, together with further objects and advantages will be better understood from the following description.

DETAILED DESCRIPTION

Figure 1:
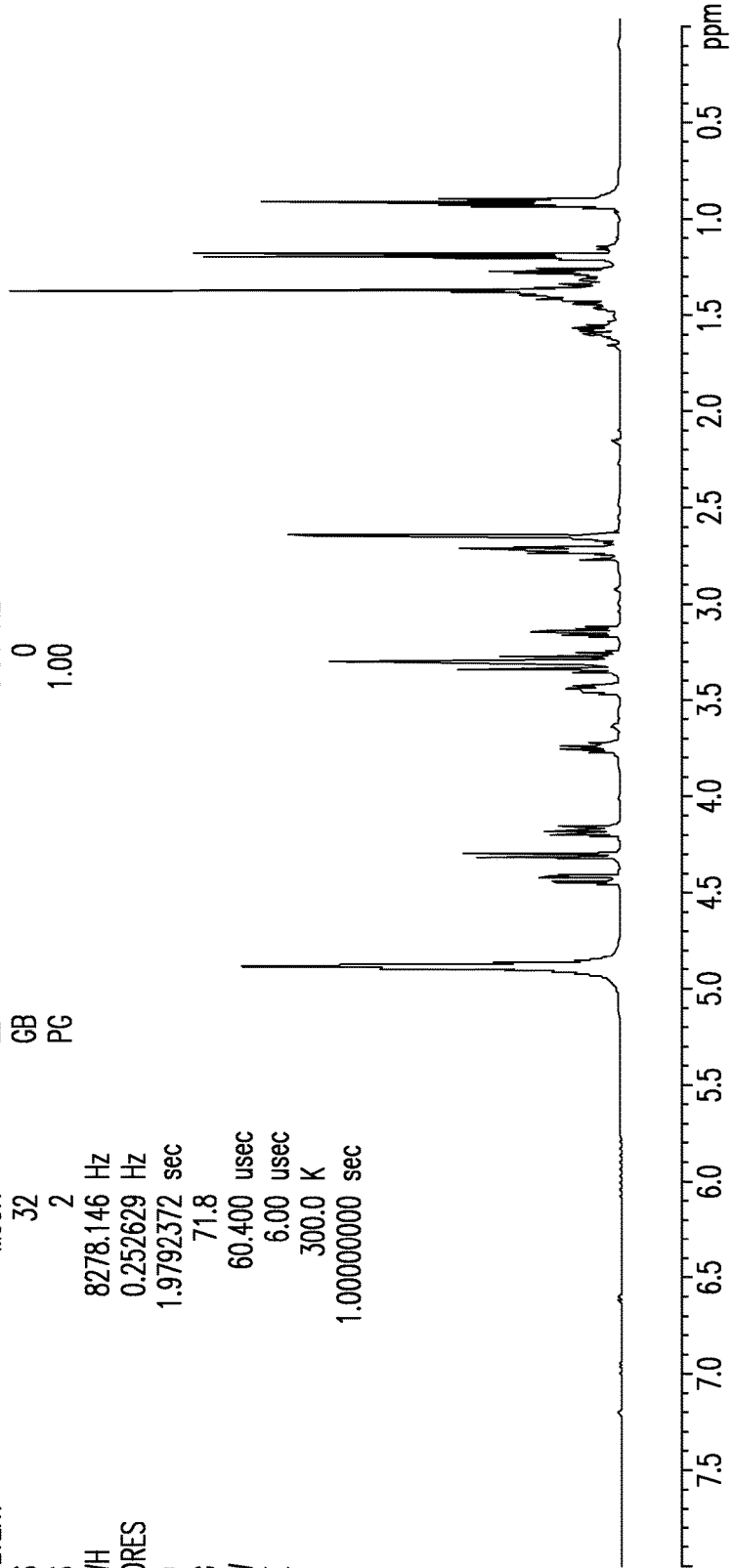
FIG. 1 shows an NMR spectrum for an isomer of Formula II synthesized according to synthesis scheme 1, as described by Example 2.
Figure 2:
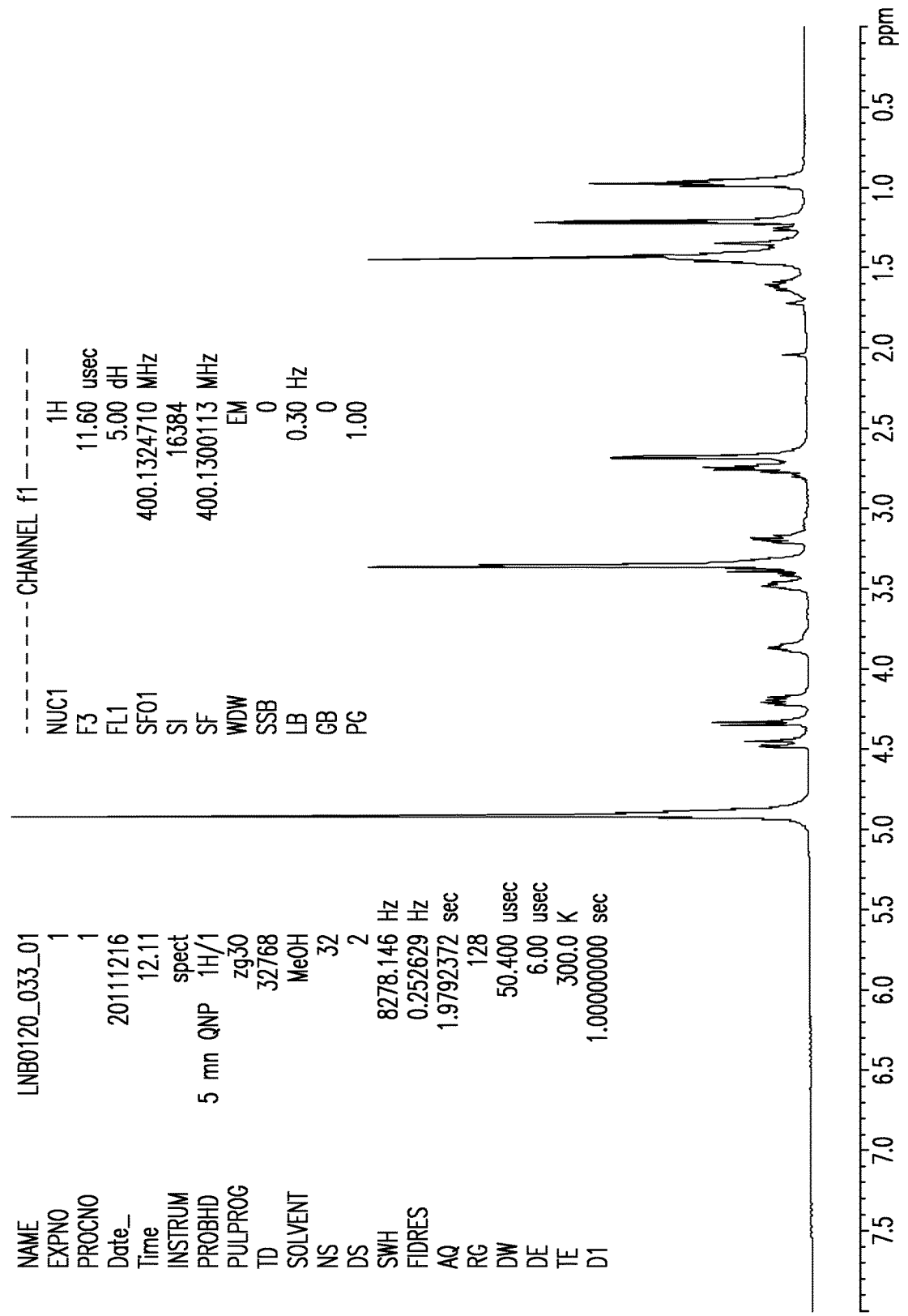
FIG. 2 shows an NMR spectrum for an isomer of Formula II synthesized according to synthesis scheme 2, as described by Example 2.

To date, there remains a need for a flavor modifier that can provide a desired level of mouth watering and/or lubricating and/or slippery and/or astringent mouthfeel in various edible compositions. The present application relates to flavor compositions that include at least one HMG glucoside compound. In certain non-limiting embodiments, the HMG glucoside comprises a compound of Formula I. The flavor compositions can be used to enhance or modify the taste and/or flavor and/or texture of various edible compositions such as sweet goods and savory goods. The flavor compositions can include combinations of compounds, and can be added to edible compositions in various delivery system formats.

1. Definitions

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having," "including," "containing" and "comprising" are interchangeable and one of skill in the art is cognizant that these terms are open ended terms.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, "taste" refers to a sensation caused by activation or inhibition of receptor cells in a subject's taste buds. In certain embodiments, taste can be selected from the group consisting of sweet, sour, salt, bitter, kokumi and umami. In certain embodiments, a taste is elicited in a subject by a "tastant." In certain embodiments, a tastant is a synthetic tastant. In certain embodiments, the tastant is prepared from a natural source.

As used herein, "taste profile" refers to a combination of tastes, such as, for example, one or more of a sweet, sour, salt, bitter, kokumi and/or umami taste. In certain embodiments, a taste profile is produced by one or more tastant that is present in a composition at the same or different concentrations. In certain embodiments, a taste profile refers to the intensity of a taste or combination of tastes, for example, a sweet, sour, salt, bitter, kokumi and/or umami taste, as detected by a subject or any assay known in the art. In certain embodiments, modifying, changing or varying the combination of tastants in a taste profile can change the sensory experience of a subject.

As used herein, "flavor" refers to one or more sensory stimuli, such as, for example, one or more of taste (gustatory), smell (olfactory), touch (tactile) and temperature (thermal) stimuli. The terms "flavor" and "aroma" are synonymous and are used interchangeably. In certain non-limiting embodiments, the sensory experience of a subject exposed to a flavor can be classified as a characteristic experience for the particular flavor. For example, a flavor can be identified by the subject as being, but not limited to, a floral, citrus, berry, nutty, caramel, chocolate, peppery, smoky, cheesy, meaty, etc. flavor As used herein, a flavor composition can be selected from a liquid, dry powder, spray, paste, suspension and any combination thereof. The flavor can be a natural composition, an artificial composition, a nature identical, or any combination thereof.

As used herein, "flavor profile" refers to a combination of sensory stimuli, for example, tastes, such as sweet, sour, bitter, salty, kokumi and/or umami tastes, and/or olfactory, tactile and/or thermal stimuli. In certain embodiments, the flavor profile comprises one or more flavors which contribute to the sensory experience of a subject. In certain embodiments, modifying, changing or varying the combination of stimuli in a flavor profile can change the sensory experience of a subject.

As used herein, "texture profile" or "mouthfeel" refers to a composition's physical and chemical interaction in the mouth. The texture profile of a composition can include one or more texture, such as, for example, but not limited to, mouth watering, lubricating, slippery, astringency, hardness, cohesiveness, viscosity, elasticity, adhesiveness, brittleness, chewiness, gumminess, moisture content, grittiness, smoothness, oiliness and greasiness. In certain embodiments, the texture profile can comprise one or more texture characteristic in the same or different intensities. In certain embodiments, the texture profile can remain constant or change during a sensory experience, for example, from initial perception of a composition on the palate, to first bite, through mastication and finally, the act of swallowing.

As used herein, "sensory experience" refers to a subject's sensory perception of a taste, taste profile, flavor, flavor profile or texture profile.

As used herein, "ppb" means parts-per-billion and is a weight relative parameter. A part-per-billion is a nanogram per gram, such that a component that is present at 10 ppb is present at 10 nanograms of the specific component per 1 gram of the aggregate mixture.

As used herein, "ppm" means parts-per-million and is a weight relative parameter. A part-per-million is a microgram per gram, such that a component that is present at 10 ppm is present at 10 micrograms of the specific component per 1 gram of the aggregate mixture.

As used herein "admixing," for example, "admixing the HMG glucoside flavor composition, or combinations thereof, of the present application with a food product," refers to the process where the flavor composition is mixed with or added to the completed product or mixed with some or all of the components of the product during product formation or some combination of these steps. When used in the context of admixing the term "product" refers to the product or any of its components. This admixing step can include a process selected from the step of adding the flavor composition to the product, spraying the flavor composition on the product, coating the flavor composition on the product, suspending the product in the flavor composition, painting the flavor composition on the product, pasting the flavor composition on the product, encapsulating the product with the flavor composition, mixing the flavor composition with the product and any combination thereof. The flavor composition can be a liquid, dry powder, spray, paste, suspension and any combination thereof.

As used herein "food product" refers to an ingestible product, such as, but not limited to, human food, animal (pet) foods, and pharmaceutical compositions.

As used herein "flavor composition" refers to at least one compound or biologically acceptable salt thereof that modulates, including enhancing, multiplying, potentiating, decreasing, suppressing, or inducing, the tastes, smells, flavors and/or textures of a natural or synthetic tastant, flavoring agent, taste profile, flavor profile and/or texture profile in an animal or a human. In certain embodiments, the flavor composition comprises a combination of compounds or biologically acceptable salts thereof. In certain embodiments, the flavor composition includes one or more excipients.

As used herein "savory flavor" refers to a savory, "mouth-watering," sensation. In certain embodiments, a savory flavor is induced by one or more combination of umami tastants, for example, MSG (monosodium glutamate) in an animal or a human.

In certain embodiments, "wet soup category" means wet/liquid soups regardless of concentration or container, including frozen soups. For the purpose of this definition "soup(s)" means a food prepared from meat, poultry, fish, vegetables, grains, fruit and/or other ingredients, cooked in a liquid which may include visible pieces of some or all of these ingredients. It may be clear (as a broth) or thick (as a chowder), smooth, pureed or chunky, ready-to-serve, semi-condensed or condensed and may be served hot or cold, as a first course or as the main course of a meal or as a between meal snack (sipped like a beverage). Soup may be used as an ingredient for preparing other meal components and may range from broths (consomme) to sauces (cream or cheese-based soups).

As used herein, "dehydrated and culinary food category" means: (i) Cooking aid products such as: powders, granules, pastes, concentrated liquid products, including concentrated bouillon, bouillon and bouillon like products in pressed cubes, tablets or powder or granulated form, which are sold separately as a finished product or as an ingredient within a product, sauces and recipe mixes (regardless of technology); (ii) Meal solution products such as: dehydrated and freeze dried soups, including dehydrated soup mixes, dehydrated instant soups, dehydrated ready-to-cook soups, dehydrated or ambient preparations of ready-made dishes, meals and single serve entrees including pasta, potato and rice dishes; and (iii) Meal embellishment products such as: condiments, marinades, salad dressings, salad toppings, dips, breading, batter mixes, shelf stable spreads, barbecue sauces, liquid recipe mixes, concentrates, sauces or sauce mixes, including recipe mixes for salad, sold as a finished product or as an ingredient within a product, whether dehydrated, liquid or frozen.

As used herein, "beverage category" means beverages, beverage mixes and concentrates, including but not limited to, alcoholic and non-alcoholic ready to drink and dry powdered beverages. Other examples of foods and beverages wherein compounds according to the application may be incorporated included by way of example carbonated and non-carbonated beverages, e.g., sodas, fruit or vegetable juices, alcoholic and non-alcoholic beverages, confectionary products, e.g., salad dressings, and other condiments, cereal, and other breakfast foods, canned fruits and fruit sauces and the like.

As used herein, "frozen food category" means chilled or frozen food products. Non-limiting examples of food products of the frozen food category include ice cream, impulse ice cream, single portion dairy ice cream, single portion water ice cream, multi-pack dairy ice cream, multi-pack water ice cream, take-home ice cream, take-home dairy ice cream, ice cream desserts, bulk ice cream, take-home water ice cream, frozen yoghurt, artisanal ice cream, frozen ready meals, frozen pizza, chilled pizza, frozen soup, frozen pasta, frozen processed red meat, frozen processed poultry, frozen processed fish/seafood, frozen vegetables, frozen processed vegetables, frozen meat substitutes, frozen potatoes, frozen bakery products and frozen desserts.

As used herein, "snack food category" generally refers to any food that can be a light informal meal including, but not limited to sweet and savory snacks and snack bars. Examples of snack foods include, but are not limited to, fruit snacks, chips/crisps, extruded snacks, tortilla/corn chips, popcorn, pretzels, nuts and other sweet and savory snacks. Examples of snack bars include, but are not limited to granola/muesli bars, breakfast bars, energy bars, fruit bars and other snack bars.

As used herein, "meat food product" refers generally to a food product made by processing the edible remains of any dead animal, including birds, fish, crustaceans, shellfish and mammals. Meat food products include, without limitation, for example, prepared beef, lamb, pork, poultry or seafood products. For example, meat food products include bologna, frankfurters, sausage, luncheon, deli slices, loaves, bacon, meatballs, fish sticks, chicken fingers, and ground meats, e.g., meatloaf, meatballs and hamburgers.

As used herein, "simulated meat food product" includes, without limitation, for example, a meat alternative, meat analog, soy burger, soy bologna, soy frankfurter, soy sausage, soy luncheon loaves, soy bacon and soy meatball.

As used herein, "food product source" refers generally to the raw products from which a food product is made. In certain embodiments, the food product source is a vegetable, fruit or any other plant material. In certain embodiments, the plant material is cacao, cocoa beans, or cocoa liquor. In other embodiments, the food product source comprises the remains of any dead animal, including birds, fish, crustaceans, shellfish and mammals.

The term "alkyl" refers to a straight or branched $C_1$-$C_{20}$ (preferably $C_1$-$C_6$) hydrocarbon group consisting solely of carbon and hydrogen atoms, containing no unsaturation, and which is attached to the rest of the molecule by a single bond, e.g., methyl, ethyl, n-propyl, 1-methylethyl (isopropyl), n-butyl, n-pentyl, 1,1-dimethylethyl (t-butyl).

The term "alkenyl" refers to a $C_2$-$C_{20}$ (preferably $C_1$-$C_4$) aliphatic hydrocarbon group containing at least one carbon-carbon double bond and which may be a straight or branched chain, e.g., ethenyl, 1-propenyl, 2-propenyl (allyl), iso-propenyl, 2-methyl-1-propenyl, 1-butenyl, 2-butenyl.

The term "cycloalkyl" denotes an unsaturated, non-aromatic mono- or multicyclic hydrocarbon ring system (containing, for example, $C_3$-$C_6$) such as cyclopropyl, cyclobutyl, cyclopentyl, cyclohexyl. Examples of multicyclic cycloalkyl groups (containing, for example, $C_6$-$C_{15}$) include perhydronapthhyl, adamantyl and norbornyl groups bridged cyclic group or sprirobicyclic groups, e.g., spiro (4,4) non-2-yl.

The term "cycloalkalkyl" refers to a cycloalkyl as defined above directly attached to an alkyl group as defined above, that results in the creation of a stable structure such as cyclopropylmethyl, cyclobutylethyl, cyclopentylethyl.

The term "alkyl ether" refers to an alkyl group or cycloalkyl group as defined above having at least one oxygen incorporated into the alkyl chain, e.g., methyl ethyl ether, diethyl ether, tetrahydrofuran.

The term "alkyl amine" refers to an alkyl group or a cycloalkyl group as defined above having at least one nitrogen atom, e.g., n-butyl amine and tetrahydrooxazine.

The term "aryl" refers to aromatic radicals having in the range of about 6 to about 14 carbon atoms such as phenyl, naphthyl, tetrahydronapthyl, indanyl, biphenyl.

The term "arylalkyl" refers to an aryl group as defined above directly bonded to an alkyl group as defined above, e.g., —CH$_2$C$_6$H$_5$, and —C$_2$H$_4$C$_6$H$_5$.

The term "heterocyclic" refers to a stable 3- to 15-membered ring radical which consists of carbon atoms and one or more, for example, from one to five, heteroatoms selected from the group consisting of nitrogen, oxygen and sulfur. For purposes of this application, the heterocyclic ring radical may be a monocyclic or bicyclic ring system, which may include fused or bridged ring systems, and the nitrogen, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heteroaromatic or heteroaryl aromatic).

The heterocyclic ring radical may be attached to the main structure at any heteroatom or carbon atom that results in the creation of a stable structure.

The term "heteroaryl" refers to a heterocyclic ring wherein the ring is aromatic.

The term "heteroarylalkyl" refers to heteroaryl ring radical as defined above directly bonded to alkyl group. The heteroarylalkyl radical may be attached to the main structure at any carbon atom from alkyl group that results in the creation of a stable structure.

The term "heterocyclyl" refers to a heterocylic ring radical as defined above. The heterocyclyl ring radical may be attached to the main structure at any heteroatom or carbon atom that results in the creation of a stable structure.

2. HMG Glucoside Compounds

The present application relates to flavor compositions that include at least one 3-hydroxy-3-methylglutaric acid (HMG) glucoside compound (HMG glucoside). The flavor compositions can be used to enhance or modify the taste and/or flavor and/or texture of various edible compositions such as sweet goods and savory goods. The flavor compositions can include combinations of compounds, and can be added to edible compositions in various delivery system formats.

In certain non-limiting embodiments, the HMG glucoside comprises a compound of Formula I having the following structure.

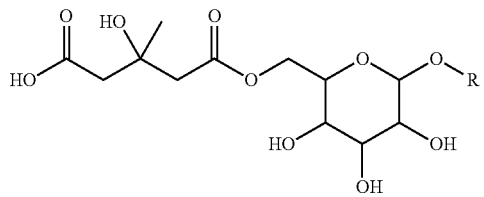

wherein R is selected from the group consisting of substituted or unsubstituted alkyl, substituted or unsubstituted alkenyl, substituted or unsubstituted cycloalkyl, substituted or unsubstituted aryl, substituted or unsubstituted cycloalkalkyl, substituted or unsubstituted arylalkyl, substituted or unsubstituted heteroarylalkyl, substituted or unsubstituted heteroaryl, substituted or unsubstituted heterocyclic, substituted or unsubstituted alkoxy, substituted or unsubstituted aryloxy, hydroxyl, hydrogen, substituted or unsubstituted ether, substituted or unsubstituted benzothiazol, substituted or unsubstituted pyridyl, substituted or unsubstituted naphthyl, substituted or unsubstituted phenyl, substituted or unsubstituted thienyl, substituted or unsubstituted benzothienyl, substituted or unsubstituted indol, substituted or unsubstituted isoquinolyl, substituted or unsubstituted quinolyl, —C(O)R$^1$ and —S(O)$_2$R$^1$, wherein R$^1$ is defined as above for R.

The substituents in the substituted groups described herein, for example, "substituted ether", "substituted alkyl", "substituted alkenyl", "substituted cycloalkyl", "substituted cycloalkalkyl", "substituted arylalkyl", "substituted aryl", "substituted heterocyclic", "substituted heteroarylalkyl," "substituted heteroaryl", "substituted naphthyl", "substituted phenyl", "substituted thienyl", "substituted benzothienyl", "substituted pyridyl", "substituted indol", "substituted isoquinolyl", "substituted quinolyl", or "substituted benzothiazol" may be the same or different with one or more selected from the groups described in the present application and hydrogen, halogen, amide, acetyl, nitro, oxo (═O), thio (═S), —NO$_2$, —CF$_3$, —OCH$_3$, -Boc or optionally substituted groups selected from alkyl, alkoxy, aryl, aryloxy, arylalkyl, ether, ester, hydroxyl, heteroaryl, and heterocyclic ring. A "substituted" functionality may have one or more than one substituent.

In one non-limiting embodiment, R is isopentyl, or an isopentyl derivative.

In certain embodiments, the compounds of the application comprise the following structure (Formula II):

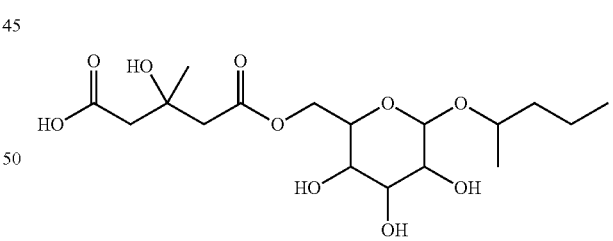

In certain embodiments, the compounds of the application comprise the following structure (Formula III):

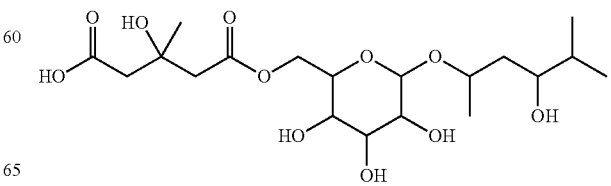

In certain embodiments, the compounds of the application comprise the following structure (Formula IV):

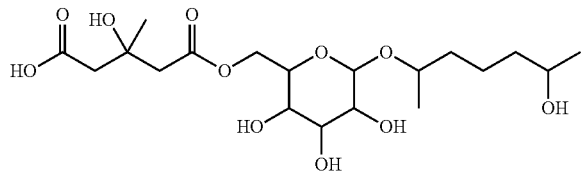 [SMILES: CC(O)CCCC(C)OC1OC(COC(=O)CC(C)(O)CC(=O)O)C(O)C(O)C1O]

In certain embodiments, the compounds of the application comprise the following structure (Formula V):

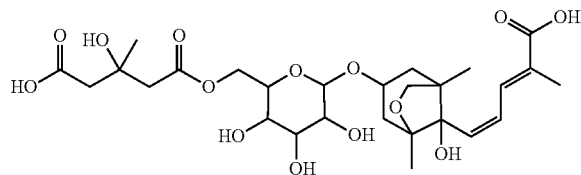 [SMILES: C/C(=C\C=C/C1(O)C2(C)COC1(C)CC(OC1OC(COC(=O)CC(C)(O)CC(=O)O)C(O)C(O)C1O)C2)C(=O)O]

In certain embodiments, the compounds of the application comprise stereoisomers of Formula I.

In certain embodiments, the compounds of the application comprise a stereoisomer of Formula II, comprising a structure selected from the group consisting of:

(Formula II-A)

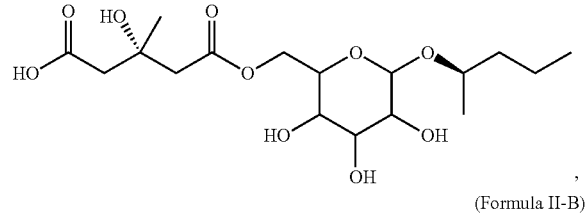
(Formula II-B)

(Formula II-C)

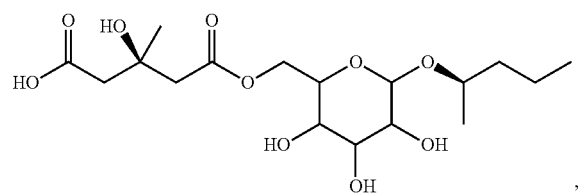

(Formula II-D)

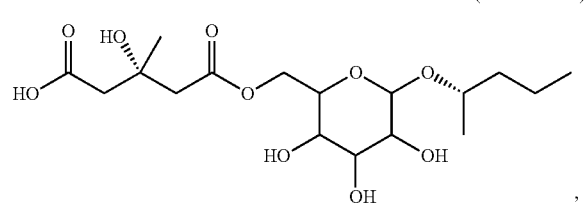

and combinations thereof.

In certain embodiments, the HMG glucoside compounds of the present application comprise a salt of the HMG glucoside, for example, but not limited to, an acetate salt, a TFA salt, or a formate salt. In certain embodiments, the HMG glucoside salt comprises an anion (−) (for example, but not limited to, $Cl^-$, $F^-$, $Br^-$, $O^{2-}$, $CO_3^{2-}$, $HCO_3^-$, $OH^-$, $NO_3^-$, $PO_4^{3-}$, $SO_4^{2-}$, $CH_3COO^-$, $HCOO^-$, $C_2O_4^{2-}$ and $CN^-$) bonded via an ionic bond with a cation (+) (for example, but not limited to, $Al^{3+}$, $Ca^{2+}$, $Na^+$, $K^+$, $Cu^{2+}$, $H^+$, $Fe^{3+}$, $Mg^{2+}$, $Ag^+$, $NH_4^+$, $H_3O^+$, $Hg_2^{2+}$). In other embodiments, the HMG glucoside salt comprises a cation (+) bonded via an ionic bond with an anion (−).

In certain embodiments, the ionic species of the HMG glucoside salt act in conjunction with other ionic tastants to modify a sensory impression of said tastants.

In certain embodiments, the HMG glucoside compound can be combined with a salt or salt mixture. The salt or salt mixture can comprise inorganic, organic, monoatomic as well as polyatomic ions. In certain embodiments, the salts are nontoxic and edible. In certain embodiments, the salt or salt mixtures are inorganic salts, for example, inorganic salts comprising halogen anions or phosphate ions, alkali or earth alkali metal salts. In certain embodiments, the salts are cationic salts such as, but not limited to, NaCl, KCl and $Na_3PO_4$. In certain embodiments, the salts are anionic salts such as, but not limited to acetate salt, TFA salt, and formate salt.

3. Flavor Compositions

The flavor compositions of the present application can be used to enhance or modify the sensory experience of various edible compositions such as sweet goods and savory goods. The flavor compositions can include combinations of compounds, and can be added to edible compositions in various delivery system formats.

In certain embodiments, the application relates to methods for modulating the texture of an edible product comprising: a) providing at least one comestible food product, or a precursor thereof, and b) combining the comestible food product or precursor thereof with at least a mouth watering, lubricating, slippery and/or astringent modulating amount of at least one flavor composition, for example, one or more HMG glucoside compound of Formula I, or a comestibly acceptable salt thereof, so as to form a modified edible food product.

In certain embodiments, the flavor compositions of the present application can enhance the mouth watering, lubricating, slippery and/or astringent texture of a food product, such as, for example, an edible composition including pet foods, pharmaceutical compositions and human foods, such as soup, a confection, and/or a snack food. In certain embodiments, the flavor compositions of the present application can be used to modify, enhance or decrease the mouth watering, lubricating, slippery and/or astringent texture of one or more of the following subgenuses of comestible compositions: confectioneries, bakery products, ice creams, dairy products, savory snacks, snack bars, meal replacement products, ready meals, soups, pastas, noodles, canned foods, frozen foods, dried foods, chilled foods, oils and fats, baby foods, or spreads, or a mixture thereof.

In certain embodiments of the application, an edible composition can be produced that contains a sufficient amount of at least one flavor composition, or its various subgenuses described herein, for example an HMG glucoside compound, for example, a compound of Formula I, to produce a composition having the desired flavor, taste and/or mouthfeel characteristics such as "mouth watering" and/or "lubricating" and/or "slippery" and/or "astringent" characteristic.

In certain embodiments of the application, an edible composition can be produced that contains a sufficient amount of at least one flavor composition, or its various subgenuses described herein, for example an HMG glucoside compound, for example a compound of Formula I, to produce a composition having the desired texture characteristics such as a "mouth watering" texture.

In certain embodiments, at least a mouth watering texture modulating amount of one or more of the flavor compositions of the present application can be added to the edible food product, so that the mouth watering texture modified edible food product has an increased or decreased mouth watering texture as compared to the edible food product prepared without the flavor composition, as determined by human beings or animals in general, or in the case of formulation testing, as determined by a taste panel of at least five human taste testers, via procedures known in the art.

In certain embodiments of the present application, the flavor composition is added to a food product in an amount effective to provide a mouth watering texture.

In certain embodiments of the application, an edible composition can be produced that contains a sufficient amount of at least one flavor composition, or its various subgenuses described herein, for example an HMG glucoside compound, for example a compound of Formula I, to produce a composition having the desired texture characteristics such as a "lubricating" texture.

In certain embodiments, at least a lubricating texture modulating amount of one or more of the flavor compositions of the present application can be added to the edible food product, so that the lubricating texture modified edible food product has an increased or decreased lubrication texture as compared to the edible food product prepared without the flavor composition, as determined by human beings or animals in general, or in the case of formulation testing, as determined by a taste panel of at least five human taste testers, via procedures known in the art.

In certain embodiments of the present application, the flavor composition is added to a food product in an amount effective to provide a lubricating texture.

In certain embodiments of the application, an edible composition can be produced that contains a sufficient amount of at least one flavor composition, or its various subgenuses described herein, for example an HMG glucoside compound, for example a compound of Formula I, to produce a composition having the desired texture characteristics such as a "slippery" texture.

In certain embodiments, at least a slippery texture modulating amount of one or more of the flavor compositions of the present application can be added to the edible food product, so that the slippery texture modified edible food product has an increased or decreased slippery texture as compared to the edible food product prepared without the flavor composition, as determined by human beings or animals in general, or in the case of formulation testing, as determined by a taste panel of at least five human taste testers, via procedures known in the art.

In certain embodiments of the present application, the flavor composition is added to a food product in an amount effective to provide a slippery texture.

In certain embodiments of the application, an edible composition can be produced that contains a sufficient amount of at least one flavor composition, or its various subgenuses described herein, for example an HMG glucoside compound, for example a compound of Formula I, to produce a composition having the desired texture characteristics such as a "astringent" texture.

In certain embodiments, at least an astringent texture modulating amount of one or more of the flavor compositions of the present application can be added to the edible food product, so that the astringent texture modified edible food product has an increased or decreased astringent texture as compared to the edible food product prepared without the flavor composition, as determined by human beings or animals in general, or in the case of formulation testing, as determined by a taste panel of at least five human taste testers, via procedures known in the art.

In certain embodiments of the present application, the flavor composition is added to a food product in an amount effective to provide a astringent texture.

In certain embodiments, the flavor composition, or any of its subgenuses, for example, an HMG glucoside, for example, a compound of Formula I, or a comestibly acceptable salt thereof, of the present application, can be combined with an edible composition in an amount effective to modify, enhance or otherwise alter a taste or taste profile of the edible composition. The modification can include, for example, an increase or decrease in one or more of a sweet, sour, salty, bitter, kokumi and/or umami taste of the composition.

In certain embodiments, the flavor composition, or any of its subgenuses, for example, an HMG glucoside, for example, a compound of Formula I, or a comestibly acceptable salt thereof, of the present application, can be combined with an edible composition in an amount effective to modify, enhance or otherwise alter a flavor or flavor profile of the edible composition. The modification can include, for example, an increase or decrease in the perception of one or more sensory stimuli, such as, for example, one or more of taste (gustatory), smell (olfactory), touch (tactile) and temperature (thermal).

In certain embodiments, the flavor composition, or any of its subgenuses, for example, an HMG glucoside, for example, a compound of Formula I, or a comestibly acceptable salt thereof, of the present application, can be combined with an edible composition in an amount effective to modify, enhance or otherwise alter a texture profile of the edible composition.

The concentration of flavor composition admixed with an edible food product to modulate or improve the flavor of the edible food product or composition can vary dependent on variables, such as, for example, the specific type of edible composition, what mouth watering, lubricating, slippery and/or astringent compounds are already present in the edible food product and the concentrations thereof, and the enhancer effect of the particular flavor composition on such mouth watering, lubricating, slippery and/or astringent compounds.

In certain embodiments, admixing the flavor compositions of the present application with an edible food product modulates, for example, induces, enhances or inhibits, the mouth watering, lubricating, slippery and/or astringent (or other taste or flavor properties) of other natural or synthetic mouth watering, lubricating, slippery and/or astringent flavorants.

A broad range of concentrations of the flavor compositions can be employed to provide such mouth watering, lubricating, slippery and/or astringent texture modification. In certain embodiments of the present application, the flavor composition is admixed with a food product wherein the flavor composition is present in an amount of from about 0.001 to about 500 ppb, or from about 0.005 to about 250 ppb, or from about 0.01 to about 200 ppb, or from about 0.05 to about 150 ppb, or from about 0.1 to about 100 ppb, or from about 0.5 to about 50 ppb.

In certain embodiments of the present application, the flavor composition is admixed with a food product wherein the flavor composition is present in an amount of from between about 0.1 to about 100 ppb.

In certain embodiments of the present application, the flavor composition is admixed with a food product wherein the flavor composition is present in an amount of from about 0.01 ppm to 5000 ppm, or narrower alternative ranges from about 0.1 ppm to about 1000 ppm, from about 0.5 ppm to about 500 ppm, from about 1 ppm to about 250 ppm, from about 5 ppm to about 200 ppm, from about 10 ppm to about 150 ppm, from about 10 ppm to about 100 ppm, or from about 20 ppm to about 50 ppm.

In certain embodiments of the present application, the flavor composition is admixed with a food product wherein the flavor composition is present in an amount of from about 0.1 ppm to about 200 ppm, or from about 1 ppm and about 150 ppm.

In certain embodiments of the present application, the flavor composition is admixed with a food product wherein the flavor composition is present in an amount of 100 ppm.

In certain embodiments of the present application, the flavor composition is admixed with a food product wherein the flavor composition is present in an amount of from about 0.0000001 to about 99.999% weight/weight (w/w), or from about 0.00005 to about 75% w/w, or from about 0.0001 to about 50% w/w, or from about 0.0005 to about 25% w/w, or from about 0.001 to about 10% w/w, or from about 0.005 to about 5% w/w of the food product.

In certain embodiments, the HMG glucoside compounds of the present application are blended together in various ratios or are blended together with other compounds to form various flavor compositions. In certain embodiments, the HMG glucoside compounds that are blended are cone or more compounds of Formula I. In certain embodiments, the HMG glucoside compounds and other compounds are blended together, wherein each of the HMG glucoside compounds and other compounds are present in an amount of from about 0.0000001 to about 99.999% weight/weight (w/w), or from about 0.00005 to about 75% w/w, or from about 0.0001 to about 50% w/w, or from about 0.0005 to about 25% w/w, or from about 0.001 to about 10% w/w, or from about 0.005 to about 5% w/w of the flavor composition.

In certain embodiments, the HMG glucoside compounds that are blended together in various ratios or are blended together with other compounds to form various flavor compositions, are, for example, compounds of Formula I of the present application. In certain embodiments, the flavor composition comprises one or more HMG glucoside compound in combination with one or more additional compound with similar solubilities as the HMG glucoside compounds. Table 1 below provides non-limiting examples of flavor compositions comprising HMG glucosides, such as a compound of Formula I, in combination with other additional compounds.

TABLE 1

| | Flavor Compositions | | | | | | | |
|---|---|---|---|---|---|---|---|---|
| Ingredient | Fl. 1 % w/w | Fl. 2 % w/w | Fl. 3 % w/w | Fl. 4 % w/w | Fl. 5 % w/w | Fl. 6 % w/w | Fl. 7 % w/w | Fl. 8 % w/w |
| Formula I | 0-99.999 | 0-99.999 | 0-99.999 | 0-99.999 | 0-99.999 | 0-99.999 | 0-99.999 | 0-99.999 |
| Formula II | 0-99.999 | 0-99.999 | 0-99.999 | 0-99.999 | 0-99.999 | 0-99.999 | 0-99.999 | 0-99.999 |
| Formula IIA | 0-99.999 | 0-99.999 | 0-99.999 | 0-99.999 | 0-99.999 | 0-99.999 | 0-99.999 | 0-99.999 |
| Formula II-B | 0-99.999 | 0-99.999 | 0-99.999 | 0-99.999 | 0-99.999 | 0-99.999 | 0-99.999 | 0-99.999 |
| Formula II-C | 0-99.999 | 0-99.999 | 0-99.999 | 0-99.999 | 0-99.999 | 0-99.999 | 0-99.999 | 0-99.999 |
| Formula II-D | 0-99.999 | 0-99.999 | 0-99.999 | 0-99.999 | 0-99.999 | 0-99.999 | 0-99.999 | 0-99.999 |
| Formula III | 0-99.999 | 0-99.999 | 0-99.999 | 0-99.999 | 0-99.999 | 0-99.999 | 0-99.999 | 0-99.999 |
| Formula IV | 0-99.999 | 0-99.999 | 0-99.999 | 0-99.999 | 0-99.999 | 0-99.999 | 0-99.999 | 0-99.999 |
| Formula V | 0-99.999 | 0-99.999 | 0-99.999 | 0-99.999 | 0-99.999 | 0-99.999 | 0-99.999 | 0-99.999 |
| Hydrolyzed cocoa powder | 0-99.999 | 0-99.999 | 0-99.999 | 0-99.999 | 0-99.999 | 0-99.999 | 0-99.999 | 0-99.999 |
| Hydrolyzed wheat protein | 0-99.999 | 0-99.999 | 0-99.999 | 0-99.999 | 0-99.999 | 0-99.999 | 0-99.999 | 0-99.999 |
| Hydrolyzed soy protein | 0-99.999 | 0-99.999 | 0-99.999 | 0-99.999 | 0-99.999 | 0-99.999 | 0-99.999 | 0-99.999 |
| Vanilla Extract | 0-99.999 | 0-99.999 | 0-99.999 | 0-99.999 | 0-99.999 | 10-18 | 0-99.999 | 0-99.999 |
| Ethyl vanillin | 0-99.999 | 0-99.999 | 0-99.999 | 0-99.999 | 12-16 | 0-99.999 | 0-99.999 | 0-99.999 |
| Ethyl maltol | 0-99.999 | 0-99.999 | 0-99.999 | 0-99.999 | 0-99.999 | 0-99.999 | 0-99.999 | 0-99.999 |
| Isoamyl acetate | 0-99.999 | 0-99.999 | 0-99.999 | 0-99.999 | 0-99.999 | 0-99.999 | 2-3 | 0-99.999 |
| Ethyl acetate | 0-99.999 | 0-99.999 | 0-99.999 | 0-99.999 | 0-99.999 | 0-99.999 | 0-99.999 | 0-99.999 |
| Furaneol | 0-99.999 | 0-99.999 | 0-99.999 | 0-99.999 | 5-8 | 0-99.999 | 0-99.999 | 0-99.999 |
| Myrcene | 0-99.999 | 0-99.999 | 0-99.999 | 0-99.999 | 0-99.999 | 0-99.999 | 1-2 | 0-99.999 |
| Linalool | 0-99.999 | 0-99.999 | 0-99.999 | 0-99.999 | 0-99.999 | 1-3 | 0-99.999 | 0-99.999 |
| Citral | 0-99.999 | 0-99.999 | 0-99.999 | 0-99.999 | 0-99.999 | 0-99.999 | 0-99.999 | 0-99.999 |
| Geraniol | 0-99.999 | 0-99.999 | 0-99.999 | 0-99.999 | 0-99.999 | 1-3 | 0-99.999 | 0-99.999 |
| NaCl | 99.5-99.9995 | 0-99.999 | 2.5-5 | 0-99.999 | 0-99.999 | 0-99.999 | 0-99.999 | 0-99.999 |
| KCl | 0-99.999 | 99.5-99.9995 | 0-99.999 | 2.5-5 | 0-99.999 | 0-99.999 | 0-99.999 | 0-99.999 |
| Garlic flavor | 0-99.999 | 0-99.999 | 14-18 | 0-99.999 | 0-99.999 | 0-99.999 | 0-99.999 | 0-99.999 |
| Onion flavor | 0-99.999 | 0-99.999 | 0-99.999 | 12-15 | 0-99.999 | 0-99.999 | 0-99.999 | 0-99.999 |
| Beef Flavor | 0-99.999 | 0-99.999 | 70-80 | 0-99.999 | 0-99.999 | 0-99.999 | 0-99.999 | 0-99.999 |
| Chicken flavor | 0-99.999 | 0-99.999 | 0-99.999 | 65-75 | 0-99.999 | 0-99.999 | 0-99.999 | 0-99.999 |
| Acetic acid | 0-99.999 | 0-99.999 | 0-99.999 | 0-99.999 | 0-99.999 | 0-99.999 | 0-99.999 | 0-99.999 |
| Butyric acid | 0-99.999 | 0-99.999 | 0-99.999 | 0-99.999 | 0-99.999 | 6-8 | 0-99.999 | 0-99.999 |
| Citric acid | 0-99.999 | 0-99.999 | 0-99.999 | 0-99.999 | 0-99.999 | 0-99.999 | 95-98 | 42-48 |
| Lactic acid | 0-99.999 | 0-99.999 | 0-99.999 | 0-99.999 | 50-65 | 70-80 | 0-99.999 | 0-99.999 |
| Malic acid | 0-99.999 | 0-99.999 | 0-99.999 | 0-99.999 | 0-99.999 | 0-99.999 | 0-99.999 | 28-32 |

TABLE 1-continued

Flavor Compositions

| Ingredient | Fl. 1 % w/w | Fl. 2 % w/w | Fl. 3 % w/w | Fl. 4 % w/w | Fl. 5 % w/w | Fl. 6 % w/w | Fl. 7 % w/w | Fl. 8 % w/w |
|---|---|---|---|---|---|---|---|---|
| Tartaric acid | 0-99.999 | 0-99.999 | 0-99.999 | 0-99.999 | 0-99.999 | 0-99.999 | 0-99.999 | 20-25 |
| Other base flavor compounds | 0-99.999 | 0-99.999 | 0-99.999 | 0-99.999 | 0-99.999 | 0-99.999 | 0-99.999 | 0-99.999 |

4. Delivery Systems

In certain embodiments, the flavor compositions of the present application can be incorporated into a delivery system for use in edible compositions. In certain embodiments, the composition will comprise another flavor, taste or texture modifier such as a mouth watering, lubricating, slippery and/or astringent flavorant. Delivery systems can be liquid or solid, aqueous or non-aqueous. Delivery systems are generally adapted to suit the needs of the flavor composition and/or the edible composition into which the flavor composition will be incorporated.

The flavoring compositions can be employed in liquid form, dried form, and/or solid form. When used in dried form, suitable drying means such as spray drying can be used. Alternatively, a flavoring composition can be encapsulated or absorbed onto water soluble materials, including but not limited to materials such as cellulose, starch, sugar, maltodextrin, gum arabic and so forth. The actual techniques for preparing such dried forms are well-known in the art, and can be applied to the presently disclosed subject matter.

The flavoring compositions of the presently disclosed subject matter can be used in many distinct physical forms well known in the art to provide an initial burst of taste, flavor and/or texture; and/or a prolonged sensation of taste, flavor and/or texture. Without being limited thereto, such physical forms include free forms, such as spray dried, powdered, and beaded forms, and encapsulated forms, and mixtures thereof.

In specific embodiments, as noted above, encapsulation techniques can be used to modify the flavor systems. In certain embodiments, flavor compounds, flavor components, or the entire flavor system can be fully or partially encapsulated. Encapsulating materials and/or techniques can be selected to determine the type of modification of the flavor system.

In specific embodiments, the encapsulating materials and/or techniques are selected to improve the stability of the flavor compounds, flavor components, or flavor systems; while in other embodiments the encapsulating materials and/or techniques are selected to modify the release profile of the flavor compounds, flavor components, or flavor systems.

Suitable encapsulating materials can include, but are not limited to, hydrocolloids such as alginates, pectins, agars, guar gums, celluloses, and the like, proteins, polyvinyl acetate, polyethylene, crosslinked polyvinyl pyrrolidone, polymethylmethacrylate, polylactidacid, polyhydroxyalkanoates, ethylcellulose, polyvinyl acetatephthalate, polyethylene glycol esters, methacrylicacid-co-methylmethacrylate, ethylene-vinylacetate (EVA) copolymer, and the like, and combinations thereof. Suitable encapsulating techniques can include, but are not limited to, spray coating, spray drying, spray chilling, absorption, adsorption, inclusion complexing (e.g., creating a flavor/cyclodextrin complex), coacervation, fluidized bed coating, or other process can be used to encapsulate an ingredient with an encapsulating material.

Encapsulated delivery systems for flavoring agents or sweetening agents contain a hydrophobic matrix of fat or wax surrounding a sweetening agent or flavoring agent core. The fats can be selected from any number of conventional materials such as fatty acids, glycerides or poly glycerol esters, sorbitol esters, and mixtures thereof. Examples of fatty acids include but are not limited to hydrogenated and partially hydrogenated vegetable oils such as palm oil, palm kernel oil, peanut oil, rapeseed oil, rice bran oil, soybean oil, cottonseed oil, sunflower oil, safflower oil, and mixtures thereof. Examples of glycerides include but are not limited to monoglycerides, diglycerides, and triglycerides.

Waxes useful can be chosen from the group consisting of natural and synthetic waxes, and mixtures thereof. Non-limiting examples include paraffin wax, petrolatum, carbowax, microcrystalline wax, beeswax, carnauba wax, candelilla wax, lanolin, bayberry wax, sugarcane wax, spermaceti wax, rice bran wax, and mixtures thereof.

The fats and waxes can be use individually or in combination in amounts varying from about 10 to about 70%, and alternatively in amounts from about 30 to about 60%, by weight of the encapsulated system. When used in combination, the fat and wax are preferably present in a ratio from about 70:10 to 85:15, respectively.

Typical encapsulated flavor compositions, flavoring agent or sweetening agent delivery systems are disclosed in U.S. Pat. Nos. 4,597,970 and 4,722,845, the disclosures of which are incorporated herein by reference in their entireties.

Liquid delivery systems can include, but are not limited to, systems with a dispersion of HMG glucoside compound(s) or the flavor compositions of the present application, such as in carbohydrate syrups and/or emulsions. Liquid delivery systems can also include extracts where the HMG glucoside compound(s) and/or the flavor compositions are solubilized in a solvent. Solid delivery systems can be created by spray drying, spray coating, spray chilling, fluidized bed drying, absorption, adsorption, coacervation, complexation, or any other standard technique. In some embodiments, the delivery system can be selected to be compatible with or to function in the edible composition. In some embodiments, the delivery system will include an oleaginous material such as a fat or oil. In some embodiments, the delivery system will include a confectionery fat such as cocoa butter, a cocoa butter replacer, a cocoa butter substitute, or a cocoa butter equivalent.

When used in dried form, suitable drying means such as spray drying may be used. Alternatively, a flavoring composition may be adsorbed or absorbed onto substrates such as water soluble materials, such as cellulose, starch, sugar, maltodextrin, gum arabic and so forth or may be encapsulated. The actual techniques for preparing such dried forms are well known in the art.

5. End Product Systems

The flavoring compositions of the present disclosed subject matter can be used in a wide variety of ingestible vehicles. Non-limiting examples of suitable ingestible vehicles include chewing gum compositions, hard and soft confections, dairy products, beverage products including juice products and soft drinks, pharmaceuticals, bakery goods, frozen foods, food products and food categories described herein. The combination of the flavoring composition of the presently disclosed subject matter together with an ingestible vehicle and optional ingredients, when desired, provides a flavoring agent that possesses unexpected taste, flavor and/or texture value and imparts, for example, a mouth watering, lubricating, slippery and/or astringent sensory experience.

In the method for flavoring an ingestible composition of the presently disclosed subject matter, the ingestible composition is prepared by admixing the flavoring agent in an ingestible vehicle, together with any optional ingredients, to form a uniform mixture. The final compositions are readily prepared using standard methods and apparatus generally known by those skilled in the corresponding arts, such as confectionary arts. The apparatus useful in accordance with the presently disclosed subject matter comprises mixing apparatus well known in the art, and therefore the selection of the specific apparatus will be apparent to the artisan.

In certain embodiments, the present application relates to the modified edible food products produced by the methods disclosed herein. In certain embodiments, the food products can be produced by processes for producing comestible products well known to those of ordinary skill in the art, wherein the flavor composition of the present application is employed as a mouth watering, lubricating, slippery and/or astringent texture enhancer for the food product.

The flavor composition and its various subgenuses can be combined with or applied to a comestible or medicinal products or precursor thereof in any of innumerable ways known to cooks the world over, or producers of comestible or medicinal products. For example, the flavor compositions can be dissolved in or dispersed in one of many known comestibly acceptable liquids, solids, or other carriers, such as water at neutral, acidic, or basic pH, fruit or vegetable juices, vinegar, marinades, beer, wine, natural water/fat emulsions such as milk or condensed milk, whey or whey products, edible oils and shortenings, fatty acids, certain low molecular weight oligomers of propylene glycol, glyceryl esters of fatty acids, and dispersions or emulsions of such hydrophobic substances in aqueous media, salts such as sodium chloride, vegetable flours, solvents such as ethanol, solid edible diluents such as vegetable powders or flours, and the like, and then combined with precursors of the comestible or medicinal products, or applied directly to the comestible or medicinal products.

In certain embodiments, the flavor compositions of the present application can be admixed with foods, beverages and other comestible compositions wherein savory compounds, especially NaCl, MSG, inosine monophosphate (IMP), or guanosine monophosphate (GMP) are conventionally utilized. These compositions include compositions for human and animal consumption, for example, food or drinks (liquids) for consumption by agricultural animals, pets and zoo animals. Those of ordinary skill in the art of preparing and selling comestible compositions (i.e., edible foods or beverages, or precursors or flavor modifiers thereof) are well aware of a large variety of classes, subclasses and species of the comestible compositions, and utilize well-known and recognized terms of art to refer to those comestible compositions while endeavoring to prepare and sell various of those comestible compositions. Such a list of terms of art is enumerated below, and it is specifically contemplated hereby that the flavor compositions of the present application can be used to modify or enhance the mouth watering, lubricating, slippery and/or astringent mouthfeel of the following list edible compositions, either singly or in all reasonable combinations or mixtures thereof.

In certain embodiments, the food products to which the flavor compositions of the present application are admixed with comprise, by way of example, the wet soup category, the dehydrated and culinary food category, the beverage category, the frozen food category, the snack food category, and seasonings or seasoning blends, described herein.

In other embodiments, the flavor compositions of the present application are admixed with one or more confectioneries, chocolate confectionery, tablets, countlines, bagged selfmies/softlines, boxed assortments, standard boxed assortments, twist wrapped miniatures, seasonal chocolate, chocolate with toys, allsorts, other chocolate confectionery, mints, standard mints, power mints, boiled sweets, pastilles, gums, jellies and chews, toffees, caramels and nougat, medicated confectionery, lollipops, liquorice, other sugar confectionery, gum, chewing gum, sugarised gum, sugar-free gum, functional gum, bubble gum, bread, packaged/industrial bread, unpackaged/artisanal bread, pastries, cakes, packaged/industrial cakes, unpackaged/artisanal cakes, cookies, chocolate coated biscuits, sandwich biscuits, filled biscuits, savory biscuits and crackers, bread substitutes, breakfast cereals, rte cereals, family breakfast cereals, flakes, muesli, other rte cereals, children's breakfast cereals, hot cereals, ice cream, impulse ice cream, single portion dairy ice cream, single portion water ice cream, multi-pack dairy ice cream, multi-pack water ice cream, take-home ice cream, take-home dairy ice cream, ice cream desserts, bulk ice cream, take-home water ice cream, frozen yoghurt, artisanal ice cream, dairy products, milk, fresh/pasteurized milk, full fat fresh/pasteurized milk, semi skimmed fresh/pasteurized milk, long-life/uht milk, full fat long life/uht milk, semi skimmed long life/uht milk, fat-free long life/uht milk, goat milk, condensed/evaporated milk, plain condensed/evaporated milk, flavored, functional and other condensed milk, flavored milk drinks, dairy only flavored milk drinks, flavored milk drinks with fruit juice, soy milk, sour milk drinks, fermented dairy drinks, coffee whiteners, powder milk, flavored powder milk drinks, cream, cheese, processed cheese, spreadable processed cheese, unspreadable processed cheese, unprocessed cheese, spreadable unprocessed cheese, hard cheese, packaged hard cheese, unpackaged hard cheese, yoghurt, plain/natural yoghurt, flavored yoghurt, fruited yoghurt, probiotic yoghurt, drinking yoghurt, regular drinking yoghurt, probiotic drinking yoghurt, chilled and shelf-stable desserts, dairy-based desserts, soy-based desserts, chilled snacks, fromage frais and quark, plain fromage frais and quark, flavored fromage frais and quark, savory fromage frais and quark, sweet and savory snacks, fruit snacks, chips/crisps, extruded snacks, tortilla/corn chips, popcorn, pretzels, nuts, other sweet and savory snacks, snack bars, granola bars, breakfast bars, energy bars, fruit bars, other snack bars, meal replacement products, slimming products, convalescence drinks, ready meals, canned ready meals, frozen ready meals, dried ready meals, chilled ready meals, dinner mixes, frozen pizza, chilled pizza, soup, canned soup, dehydrated soup, instant soup, chilled soup, uht soup, frozen soup, pasta, canned pasta, dried pasta, chilled/fresh pasta, noodles, plain noodles, instant noodles, cups/bowl instant noodles, pouch instant noodles, chilled noodles, snack noodles, canned food, canned meat and meat products, canned fish/seafood, canned vegetables, canned tomatoes, canned beans, canned fruit, canned ready meals, canned soup, canned pasta, other canned foods, frozen food, frozen processed red meat, frozen processed poultry, frozen processed fish/seafood, frozen processed vegetables, frozen meat substitutes, frozen potatoes, oven baked potato chips, other oven baked potato products, non-oven frozen potatoes, frozen bakery products, frozen desserts, frozen ready meals, frozen pizza, frozen soup, frozen noodles, other frozen food, dried food, dessert mixes, dried ready meals, dehydrated soup, instant soup, dried pasta, plain noodles, instant noodles, cups/bowl instant noodles, pouch instant noodles, chilled food, chilled processed meats, chilled fish/seafood products, chilled processed fish, chilled coated fish, chilled smoked fish, chilled lunch kit, chilled ready meals, chilled pizza, chilled soup, chilled/fresh pasta, chilled noodles, oils and fats, olive oil, vegetable and Seed oil, cooking fats, butter, margarine, spreadable oils and fats, functional spreadable oils and fats, sauces, dressings and condiments, tomato pastes and purees, bouillon/stock cubes, stock cubes, gravy granules, liquid stocks and fonds, herbs and spices, fermented sauces, soy based sauces, pasta sauces, wet sauces, dry sauces/powder mixes, ketchup, mayonnaise, regular mayonnaise, mustard, salad dressings, regular salad dressings, low fat salad dressings, vinaigrettes, dips, pickled products, other sauces, dressings and condiments, baby food, milk formula, standard milk formula, follow-on milk formula, toddler milk formula, hypoallergenic milk formula, prepared baby food, dried baby food, other baby food, spreads, jams and preserves, honey, chocolate spreads, nut-based spreads, and yeast-based spreads.

5.1 Sweet Goods 5.1.1 Chewing Gum

The flavor systems can be used in sugarless gum formulations and can also be used in a sugar chewing gum. The flavor systems can be used in either regular chewing gum or bubble gum. Various specifics of chewing gum compositions are disclosed in U.S. Pat. No. 6,899,911, the disclosure of which is incorporated herein by reference in its entirety.

The chewing gum composition of the presently disclosed subject matter follows the general pattern outlined below. In general, a chewing gum composition typically contain a chewable gum base portion which is essentially free of water and is water-insoluble, a water-soluble bulk portion and flavors which are typically water insoluble. The water-soluble portion dissipates with a portion of the flavor over a period of time during chewing. The gum base portion is retained in the mouth throughout the chew.

The insoluble gum base generally comprises elastomers, elastomer solvents, plasticizers, waxes, emulsifiers and inorganic fillers. Plastic polymers, such as polyvinyl acetate, which behave somewhat as plasticizers, are also often included. Other plastic polymers that can be used include polyvinyl laureate, polyvinyl alcohol and polyvinyl pyrrolidone.

Elastomers can include polyisobutylene, butyl rubber, (isobutylene-isoprene copolymer) and styrene butadiene rubber, as well as natural latexes such as chicle. Elastomer solvents are often resins such as terpene resins. Plasticizers, sometimes called softeners, are typically fats and oils, including tallow, hydrogenated and partially hydrogenated vegetable oils, and cocoa butter. Commonly employed waxes include paraffin, microcrystalline and natural waxes such as beeswax and carnauba. Microcrystalline waxes, especially those with a high degree of crystallinity, can be considered bodying agents or textural modifiers.

According to the preferred embodiment of the presently disclosed subject matter, the insoluble gum base constitutes between about 5% to about 95% by weight of the gum. More preferably the insoluble gum base comprises between 10% and 50% by weight of the gum and most preferably about 20% to 35% by weight of the gum.

The gum base typically also includes a filler component. The filler component can be calcium carbonate, magnesium carbonate, talc, dicalcium phosphate or the like. The filler can constitute between about 5% and about 60% by weight of the gum base. Preferably the filler comprises about 5% to 50% by weight of the gum base.

Gum bases typically also contain softeners including glycerol monostearate and glycerol triacetate. Gum bases can also contain optional ingredients such as antioxidants, colors, and emulsifiers. The presently disclosed subject matter contemplates employing any commercially acceptable gum base.

The water-soluble portion of the chewing gum can further comprise softeners, sweeteners, flavors, physiological cooling agents and combinations thereof. The sweeteners often fulfill the role of bulking agents in the gum. The bulking agents typically comprise about 5% to about 95% of the gum composition.

Softeners are added to the chewing gum in order to optimize the chewability and mouth feel of the gum. Softeners, also known in the art as plasticizers or plasticizing agents, generally constitute between about 0.5% to about 15% of the chewing gum. Softeners contemplated by the presently disclosed subject matter include glycerin, lecithin and combinations thereof. Further, aqueous sweetener solutions such as those containing sorbitol, hydrogenated starch hydrolysate, corn syrup and combinations thereof can be used as softeners and binding agents in gum.

As mentioned above, the flavor systems of the presently disclosed subject matter can be used in sugarless gum formulations. However, formulations containing sugar are also within the scope of the invention. Sugar sweeteners generally include saccharide-containing components commonly known in the chewing gum art which comprise, but are not limited to, sucrose, dextrose, maltose, dextrin, dried invert sugar, fructose, galactose, corn syrup solids and the like, alone or in any combination.

The flavor systems of the presently disclosed subject matter can also be used in combination with sugarless sweeteners. Generally sugarless sweeteners include components with sweetening characteristics but which are devoid of the commonly known sugars and comprise, but are not limited to, sugar alcohols such as sorbitol, hydrogenated isomaltulose, mannitol, xylitol, lactitol, erythritol, hydrogenated starch hydrolysate, maltitol and the like alone or in any combination Depending on the particular sweetness release profile and shelf-stability needed, coated or uncoated high-intensity sweeteners can be used in the chewing gum composition, or can be used in a coating applied to centers made from those gum compositions. High-intensity sweeteners, preferably aspartame, can be used at levels from about 0.01% to about 3.0%. Encapsulated aspartame is a high intensity sweetener with improved stability and release characteristics, as compared to free aspartame. Free aspartame can also be added, and a combination of some free and encapsulated aspartame is preferred when aspartame is used. Other high intensity sweeteners that can be used in the gum center are: saccharin, Thaumatin, alitame, saccharin salts, sucralose, Stevia, and acesulfame K. Overall, the chewing gum composition will preferable comprise about 0.5% to about 90% sweetening agents. Most typically the sweetening agents will comprises at least one bulk sweetener and at least one high-intensity sweetener.

Optional ingredients such as colors, emulsifiers and pharmaceutical agents can also be added as separate components of the chewing gum composition, or added as part of the gum base.

Aqueous syrups, such as corn syrup and hydrogenated corn syrup can be used, particularly if their moisture content is reduced. This can preferably be done by coevaporating the aqueous syrup with a plasticizer, such as glycerin or propylene glycol, to a moisture content of less than 10%. Preferred compositions include hydrogenated starch hydrolysate solids and glycerin. Such syrups and their methods of preparation are discussed in detail in U.S. Pat. No. 4,671, 967.

A preferred method of manufacturing chewing gum according to the presently disclosed subject matter is by sequentially adding the various chewing gum ingredients to any commercially available mixer known in the art. After the ingredients have been thoroughly mixed, the gum is discharged from the mixer and shaped into the desired form such as by rolling into sheets and cutting into sticks, extruding into chunks, or casting into pellets.

Generally, the ingredients are mixed by first melting the gum base and adding it to the running mixer. The base can also be melted in the mixer itself. Color or emulsifiers can also be added at this time, along with syrup and a portion of the bulking agent. Further portions of the bulking agent can then be added to the mixer. Flavor systems are typically added with the final portion of the bulking agent. If the flavor system is coated or otherwise modified as when incorporated into a delivery system to modify its release rate, it will preferably be added after the final portion of bulking agent has been added. The entire mixing procedure typically takes from five to twenty minutes, but longer mixing times can sometime be required. Those skilled in the art will recognize that many variations of the above described procedures can be followed.

If formed into pellets or balls, the chewing gum composition can be coated. The coating is initially present as a liquid syrup which contains from about 30% to about 80% or 85% sugars or sugar alcohols, and from about 15% or 20% to about 70% of a solvent such as water. In general, the coating process is carried out in conventional panning equipment. Gum center tablets to be coated are placed into the panning equipment to form a moving mass.

The material or syrup which will eventually form the coating is applied or distributed over the gum center tablets. The flavor systems of the presently disclosed subject matter can be added before, during and after applying the syrup to the gum centers. Once the coating has dried to form a hard surface, additional syrup additions can be made to produce a plurality of coatings or multiple layers of coating. The flavor systems can be added to any or none of the coatings and/or layers.

In the panning procedure, syrup is added to the gum center tablets at a temperature range of from about 100° F. to about 240° F. Preferably, the syrup temperature is from about 140° F. to about 200° F. Most preferably, the syrup temperature should be kept constant throughout the process in order to prevent the polyol in the syrup from crystallizing.

The syrup can be mixed with, sprayed upon, poured over, or added to the gum center tablets in any way known to those skilled in the art.

In another embodiment, a soft coating is formed by adding a powder coating after a liquid coating. The powder coating can include natural carbohydrate gum hydrolysates, maltodextrin, gelatin, cellulose derivatives, starches, modified starches, sugars, sugar alcohols, natural carbohydrate gums and fillers like talc and calcium carbonate.

Each component of the coating on the gum center can be applied in a single layer or in a plurality of layers. In general, a plurality of layers is obtained by applying single coats, allowing the layers to dry, and then repeating the process. The amount of solids added by each coating step depends chiefly on the concentration of the coating syrup. Any number of coats can be applied to the gum center tablet. Preferably, no more than about 75 coats are applied to the gum center. More preferably, less than about 60 coats are applied and most preferably, about 30 to about 60 coats are applied. In any event, the presently disclosed subject matter contemplates applying an amount of syrup sufficient to yield a coated chewing gum product containing about 10% to about 65% coating. Preferably, the final product will contain from about 20% to about 50% coating.

Those skilled in the art will recognize that in order to obtain a plurality of coated layers, a plurality of premeasured aliquots of coating syrup can be applied to the gum center. It is contemplated, however, that the volume of aliquots of syrup applied to the gum center can vary throughout the coating procedure.

Once a coating of syrup is applied to the gum center, the syrup is dried in an inert medium. A preferred drying medium comprises air. Preferably, forced drying air contacts the wet syrup coating in a temperature range of from about 70° F. to about 110° F. More preferably, the drying air is in the temperature range of from about 80° F. to about 100° F. The invention also contemplates that the drying air possesses a relative humidity of less than about 15 percent. Preferably, the relative humidity of the drying air is less than about 8%.

The drying air can be passed over and admixed with the syrup coated gum centers in any way commonly known in the art. Preferably, the drying air is blown over and around the syrup coated gum center at a flow rate, for large scale operations, of about 2800 cubic feet per minute. If lower quantities of material are being processed, or if smaller equipment is used, lower flow rates would be used. If a flavor is applied after a syrup coating has been dried, the presently disclosed subject matter contemplates drying the flavor with or without the use of a drying medium.

The amount of flavoring agent employed herein is normally a matter of preference subject to such factors as the type of final chewing gum composition, the individual flavor, the gum base employed, and the strength of flavor desired. Thus, the amount of flavoring can be varied in order to obtain the result desired in the final product and such variations are within the capabilities of those skilled in the art without the need for undue experimentation. In gum compositions, the flavoring agent is generally present in amounts from about 0.02% to about 5%, and preferably from about 0.1% to about 2%, and more preferably, from about 0.8% to about 1.8%, by weight of the chewing gum composition.

5.1.2 Sugar Confectionary

Another important aspect of the presently disclosed subject matter includes a confectionery composition incorporating the inventive flavoring agent and a method for preparing the confectionery compositions. The preparation of confectionery formulations is well-known in the art. Confectionery items have been classified as either "hard" confectionery or "soft" confectionery. The flavoring agents of the presently disclosed subject matter can be incorporated into the confections by admixing the compositions of the presently disclosed subject matter into the conventional hard and soft confections.

Hard confectionery can be processed and formulated by conventional means. In general, a hard confectionery has a base composed of a mixture of sugar and other carbohydrate bulking agents kept in an amorphous or glassy condition. The hard confectionery can also be sugarless. This form is considered a solid syrup of sugars generally having from about 0.5% to about 1.5% moisture. Such materials normally contain up to about 92% sugar, up to about 55% corn syrup and from about 0.1% to about 5% water, by weight of the final composition. The syrup component is generally prepared from sucrose and corn syrups, but can include other materials. Further ingredients such as flavorings, sweetening agents, acidulants, colorants and so forth can also be added.

Such confectionery can be routinely prepared by conventional methods, including but not limited to methods involving fire cookers, vacuum cookers, and scraped-surface cookers also referred to as high speed atmospheric cookers. The apparatus useful in accordance with the presently disclosed subject matter comprises cooking and mixing apparatus well known in the confectionery manufacturing arts, and therefore the selection of the specific apparatus will be apparent to the artisan.

Fire cookers involve the traditional method of making a candy base. In this method, the desired quantity of carbohydrate bulking agent is dissolved in water by heating the agent in a kettle until the bulking agent dissolves. Additional bulking agent can then be added and cooked until a final temperature of 145° C. to 156° C. is achieved. The batch is then cooled and worked as a plastic-like mass to incorporate additives such as flavoring agent, colorants and the like.

A high-speed atmospheric cooker uses a heat-exchanger surface, which involves spreading a film of candy on a heat exchange surface, the candy is heated to 165° C. to 170° C. within a few seconds. The candy is then rapidly cooled to 100° C. to 120° C. and worked as a plastic-like mass enabling incorporation of the additives, such as flavoring agent, colorants and the like. In vacuum cookers, the carbohydrate bulking agent is boiled to 125° C. to 132° C., vacuum is applied and additional water is boiled off without extra heating. When cooking is complete, the mass is a semi-solid and has a plastic-like consistency. At this point, flavoring agent, colorants, and other additives are admixed in the mass by routine mechanical mixing operations.

The optimum mixing required to uniformly mix the flavoring agent, colorants and other additives during conventional manufacturing of hard confectionery is determined by the time needed to obtain a uniform distribution of the materials. Generally, mixing times of from 2 to 10 minutes have been found to be acceptable.

Once the candy mass has been properly tempered, it can be cut into workable portions or formed into desired shapes. A variety of forming techniques can be utilized depending upon the shape and size of the final product desired. A general discussion of the composition and preparation of hard confections can be found in H. A. Lieberman, Pharmaceutical Dosage Forms: Tablets, Volume 1 (1989), Marcel Dekker, Inc., New York, N.Y. at pages 419 to 582, which disclosure is incorporated herein by reference.

Compressed tablet confections contain particular materials and are formed into structures under pressure. These confections generally contain sugars in amounts up to about 95%, by weight of the composition, and typical tablet excipients such as binders and lubricants as well as flavoring agent, colorants and so forth. These confections can also be sugarless.

Similar to hard confectionery, soft confectionery can be utilized in the embodiments of the disclosed subject matter. The preparation of soft confections, such as nougat, involves conventional methods, such as the combination of two primary components, namely (1) a high boiling syrup such as a corn syrup, or the like, and (2) a relatively light textured frappe, generally prepared from egg albumin, gum arabic, gelatin, vegetable proteins, such as soy derived compounds, sugarless milk derived compounds such as milk proteins, and mixtures thereof. The frappe is generally relatively light, and can, for example, range in density from about 0.5 to about 0.7 grams/cc.

The high boiling syrup, or "bob syrup" of the soft confectionery is relatively viscous and has a higher density than the frappe component, and frequently contains a substantial amount of carbohydrate bulking agent. Conventionally, the final nougat composition is prepared by the addition of the "bob syrup" to the frappe under agitation, to form the basic nougat mixture. Further ingredients such as flavoring, additional carbohydrate bulking agent, colorants, preservatives, medicaments, mixtures thereof and the like can be added thereafter also under agitation. Soft confectioneries can also be prepared sugarless. A general discussion of the composition and preparation of nougat confections can be found in B. W. Minifie, Chocolate, Cocoa and Confectionery: Science and Technology, 2nd edition, AVI Publishing Co., Inc., Westport, Conn. (1983), at pages 576-580, which disclosure is incorporated herein by reference.

In general, the frappe component is prepared first and thereafter the syrup component is slowly added under agitation at a temperature of at least about 65° C., and preferably at least about 100° C. The mixture of components is continued to be mixed to form a uniform mixture, after which the mixture is cooled to a temperature below 80° C., at which point, the flavor can be added. The mixture is further mixed for an additional period until it is ready to be removed and formed into suitable confectionery shapes.

In accordance with this invention, effective amounts of the flavoring agents of the presently disclosed subject matter can be admixed into the hard and soft confections. The exact amount of flavoring agent employed is normally a matter of preference subject to such factors as the particular type of confection being prepared, the type of bulking agent or carrier employed, the type of flavor employed and the intensity of breath freshening perception desired. Thus, the amount of flavoring agent can be varied in order to obtain the result desired in the final product and such variations are within the capabilities of those skilled in the art without the need for undue experimentation. In general, the amount of flavoring agent normally present in a hard or soft confection will be from about 0.001% to about 20%, preferably from about 0.01% to about 15%, more preferably from about 0.01% to about 10%, and more preferably from about 0.01% to about 5%, and more preferably 0.01% to about 0.5% by weight of the confection.

The presently disclosed subject matter extends to methods for making the improved confections. The flavoring agents can be incorporated into an otherwise conventional hard or soft confection composition using standard techniques and equipment known to those skilled in the art. The apparatus useful in accordance with the presently disclosed subject matter comprises mixing and heating apparatus well known in the confectionery manufacturing arts, and therefore the selection of the specific apparatus will be apparent to the artisan.

In such a method, a composition is made by admixing the inventive flavoring agent into the confectionery composition along with the other ingredients of the final desired composition. Other ingredients will usually be incorporated into the composition as dictated by the nature of the desired composition as well known by those having ordinary skill in the art. The ultimate confectionery compositions are readily prepared using methods generally known in the food technology and pharmaceutical arts. Thereafter the confectionery mixture can be formed into desirable confectionery shapes.

The flavoring agents can be formulated with conventional ingredients which offer a variety of textures to suit particular applications. Such ingredients can be in the form of hard and soft confections, tablets, toffee, nougat, chewy candy, chewing gum and so forth, center filled candies, both sugar and sugarless. The acceptable ingredients can be selected from a wide range of materials. Without being limited thereto, such materials include diluents, binders and adhesives, lubricants, disintegrants, bulking agents, humectants and buffers and adsorbents. The preparation of such confections and chewing gum products is well known.

5.1.3. Chocolates and Fillings

The presently disclosed subject matter is also used with and/or in chocolate products, chocolate-flavored confections, and chocolate flavored compositions. Chocolates also include those containing crumb solids or solids fully or partially made by a crumb process. Various chocolates are disclosed, for example, in U.S. Pat. Nos. 7,968,140 and 8,263,168, the disclosures of which are incorporated herein by reference in their entireties. A general discussion of the composition and preparation of chocolate confections can be found in B. W. Minifie, Chocolate, Cocoa and Confectionery: Science and Technology, 2nd edition, AVI Publishing Co., Inc., Westport, Conn. (1982), which disclosure is incorporated herein by reference.

The term "chocolate" as used herein refers to a solid or semi-plastic food and is intended to refer to all chocolate or chocolate-like compositions containing a fat-based component phase or fat-like composition. The term is intended to include standardized or nonstandardized compositions conforming to the U.S.

Standards Of Identity (SOI), CODEX Alimentarius and/or other international standards and compositions not conforming to the U.S. Standards Of Identity or other international standards. The term includes dark chocolate, baking chocolate, sweet chocolate, bittersweet or semisweet chocolate, milk chocolate, buttermilk chocolate, skim milk chocolate, mixed dairy product chocolate, white chocolate, sweet cocoa and vegetable fat coating, sweet chocolate and vegetable fat coating, milk chocolate and vegetable fat coating, vegetable fat based coating, pastels including white chocolate or coating made with cocoa butter or vegetable fat or a combination of these, nutritionally modified chocolate-like compositions (chocolates or coatings made with reduced calorie ingredients) and low fat chocolates, aerated chocolates, compound coatings, non-standardized chocolates and chocolate-like compositions, unless specifically identified otherwise.

Nonstandardized chocolates result when, for example, the nutritive carbohydrate sweetener is replaced partially or completely; or when the cocoa butter, cocoa butter alternative, cocoa butter equivalent, cocoa butter extender, cocoa butter replacer, cocoa butter substitute or milkfat are replaced partially or completely; or when components that have flavors that imitate milk, butter or chocolate are added or other additions or deletions in formula are made outside the FDA standards of identify of chocolate or combinations thereof. Chocolate-like compositions are those fat-based compositions that can be used as substitutes for chocolate in applications such as panning, molding, or enrobing; for example, carob.

In the United States, chocolate is subject to a standard of identity established by the U.S. Food and Drug Administration (FDA) under the Federal Food, Drug and Cosmetic Act. Definitions and standards for the various types of chocolate are well established in the U.S. Nonstandardized chocolates are those chocolates which have compositions that fall outside the specified ranges of the standardized chocolates.

The chocolate can contain a sugar syrup/solids, invert sugar, hydrolyzed lactose, maple sugar, brown sugar, molasses, honey, sugar substitute and the like. The term "sugar substitute" includes bulking agents, sugar alcohols (polyols such as glycerol), or high potency sweeteners or combinations thereof. Nutritive carbohydrate sweeteners with varying degrees of sweetness intensity can be any of those typically used in the art and include, but are not limited to, sucrose, e.g. from cane or beet, dextrose, fructose, lactose, maltose, glucose syrup solids, corn syrup solids, invert sugar, hydrolyzed lactose, honey, maple sugar, brown sugar, molasses and the like. Sugar substitutes can partially replace the nutritive carbohydrate sweetener. High potency sweeteners include aspartame, cyclamates, saccharin, acesulfame-K, neohesperidin dihydrochalcone, sucralose, alitame, stevia sweeteners, glycyrrhizin, thaumatin and the like and mixtures thereof. The preferred high potency sweeteners are aspartame, cyclamates, saccharin, and acesulfame-K. Examples of sugar alcohols can be any of those typically used in the art and include sorbitol, mannitol, xylitol, maltitol, isomalt, lactitol and the like.

The chocolates can also contain bulking agents. The term "bulking agents" as defined herein can be any of those typically used in the art and include polydextrose, cellulose and its derivatives, maltodextrin, gum arabic, and the like.

The chocolate products can contain emulsifiers. Examples of safe and suitable emulsifiers can be any of those typically used in the art and include lecithin derived from vegetable sources such as soybean, safflower, corn, etc., fractionated lecithins enriched in either phosphatidyl choline or phosphatidyl ethanolamine, or both, mono- and digylcerides, diacetyl tartaric acid esters of mono- and diglycerides (also referred to as DATEM), monosodium phosphate derivatives of mono- and diglycerides of edible fats or oils, sorbitan monostearate, hydroxylated lecithin, lactylated fatty acid esters of glycerol and propylene glycol, polyglycerol esters of fatty acids, propylene glycol mono- and di-esters of fats and fatty acids, or emulsifiers that can become approved for the US FDA-defined soft candy category. In addition, other emulsifiers that can be used include polyglycerol polyricinoleate (PGPR), ammonium salts of phosphatidic acid, (e.g. YN) sucrose esters, oat extract, etc., any emulsifier found to be suitable in chocolate or similar fat/solid system or any blend.

The term "chocolate-flavored confection" refers to food products, excluding "chocolate", having a chocolate flavor/aroma and comprising a cocoa fraction. These products are stable at ambient temperatures for extended periods of time (e.g., greater than 1 week) and are characterized as microbiologically shelf-stable at 18-30° C. under normal atmospheric conditions. Examples include chocolate-flavored hard candies, chewables, chewing gums, etc.

The term "chocolate-flavored compositions" refers to chocolate-flavored compositions, excluding "chocolate", containing a cocoa fraction and having a chocolate flavor/aroma. Examples include chocolate-flavored cake mixes, ice creams, syrups, baking goods, etc. The term includes chocolate-flavored compositions (e.g., cakes, nougats, puddings, etc.), as well as compositions not having a chocolate-flavor (e.g., caramels, etc.).

5.2 Savory Goods and Other Food Products

In certain embodiments, the flavor compositions of the present application are incorporated into savory goods to impart, enhance, or modify a mouth watering, lubricating, slippery and/or astringent mouthfeel. In certain embodiments, a savory good is a food product that has savory flavors including, for example, but not limited to, spicy flavor, pepper flavor, dairy flavor, vegetable flavor, tomato flavor, dill flavor, meat flavor, poultry flavor, chicken flavor and reaction flavors that are added or generated during heating of a food product.

In certain embodiments, the flavor compositions are incorporated into a wet soup category food product, which comprises wet/liquid soups regardless of concentration or container, including frozen soups. In certain embodiments, the a soup food product means a food prepared from meat, poultry, fish, vegetables, grains, fruit and/or other ingredients, cooked in a liquid which may include visible pieces of some or all of these ingredients. It may be clear (as a broth) or thick (as a chowder), smooth, pureed or chunky, ready-to-serve, semi-condensed or condensed and may be served hot or cold, as a first course or as the main course of a meal or as a between meal snack (sipped like a beverage). Soup may be used as an ingredient for preparing other meal components and may range from broths (consomme) to sauces (cream or cheese-based soups).

In certain embodiments, the flavor compositions of the present application are incorporated into a dehydrated and culinary food category of food products, which comprises (i) cooking aid products such as: powders, granules, pastes, concentrated liquid products, including concentrated bouillon, bouillon and bouillon like products in pressed cubes, tablets or powder or granulated form, which are sold separately as a finished product or as an ingredient within a product, sauces and recipe mixes (regardless of technology); (ii) meal solutions products such as: dehydrated and freeze dried soups, including dehydrated soup mixes, dehydrated instant soups, dehydrated ready-to-cook soups, dehydrated or ambient preparations of ready-made dishes, meals and single serve entrees including pasta, potato and rice dishes; and (iii) meal embellishment products such as: condiments, marinades, salad dressings, salad toppings, dips, breading, batter mixes, shelf stable spreads, barbecue sauces, liquid recipe mixes, concentrates, sauces or sauce mixes, including recipe mixes for salad, sold as a finished product or as an ingredient within a product, whether dehydrated, liquid or frozen.

In certain embodiments, the flavor compositions of the present application are incorporated into a meat food product. In certain embodiments, meat food products include food product made by processing the edible remains of any dead animal, including birds, fish, crustaceans, shellfish and mammals. Meat food products include, without limitation, for example, prepared beef, lamb, pork, poultry or seafood products. Examples of such meat food products include, for example, bologna, frankfurters, sausage, luncheon, deli slices, loaves, bacon, meatballs, fish sticks, chicken fingers, and ground meats, e.g., meatloaf, meatballs and hamburgers. A meat food product may be combined with a simulated meat food product. Simulated meat food products include, without limitation, for example, a meat alternative, meat analog, soy burger, soy bologna, soy frankfurter, soy sausage, soy luncheon loaves, soy bacon and soy meatball. A simulated meat food product may be combined with a meat food product.

In certain embodiments, the flavor compositions of the present application are incorporated into a snack food category food product. In certain embodiments, snack food products include any food that can be a light informal meal including, but not limited to sweet and savory snacks and snack bars. Examples of snack food include, but are not limited to fruit snacks, chips/crisps, extruded snacks, tortilla/corn chips, popcorn, pretzels, nuts and other sweet and savory snacks.

Examples of snack bars include, but are not limited to granola/muesli bars, breakfast bars, energy bars, fruit bars and other snack bars In certain embodiments, the flavor compositions of the present application are incorporated into frozen of food products, which comprises chilled or frozen food products, for example, but not limited to, ice cream, impulse ice cream, single portion dairy ice cream, single portion water ice cream, multi-pack dairy ice cream, multi-pack water ice cream, take-home ice cream, take-home dairy ice cream, ice cream desserts, bulk ice cream, take-home water ice cream, frozen yoghurt, artisanal ice cream, frozen ready meals, frozen pizza, chilled pizza, frozen soup, frozen pasta, frozen processed red meat, frozen processed poultry, frozen processed fish/seafood, frozen processed vegetables, frozen meat substitutes, frozen potatoes, frozen bakery products and frozen desserts.

In certain embodiments, the flavor compositions of the present application are incorporated into food products for animal consumption. This includes food or drinks (liquids) for consumption by agricultural animals, pets and zoo animals.

The presently disclosed subject matter can be used in a variety of food products. The term "food product" includes any food product, for example, those set forth in 21 CFR 101.12. Nonlimiting examples of such food products include frozen desserts, baked goods, fillings, nutritional drinks, beverages, salad dressing or similar dressing, sauces, icings, puddings and custards, batters, and the like. Various baked goods are disclosed in U.S. Pat. No. 6,536,599, the disclosure of which is herein incorporated by reference in its entirety. Non-limiting examples of bakery goods includes cookies, cakes, rolls, pastries, pie dough, brownies, breads, bagels and the like. The flavor compositions are also suitable as a component in frozen foods.

5.3 Pharmaceuticals

The flavoring compositions can also be in the form of a pharmaceutical. One nonlimiting example of a pharmaceutical form is a suspension. Pharmaceutical suspensions can be prepared by conventional compounding methods. Suspensions can contain adjunct materials employed in formulating the suspensions of the art. The suspensions of the presently disclosed subject matter can comprise preservatives, buffers, suspending agents, antifoaming agents, sweetening agents, flavoring agents, coloring or decoloring agents, solubilizers, and combinations thereof.

Flavoring agents such as those flavors well known to the skilled artisan, such as natural and artificial flavors and mints, such as peppermint, menthol, citrus flavors such as orange and lemon, artificial vanilla, cinnamon, various fruit flavors, both individual and mixed and the like can be utilized in amounts from about 0.01% to about 5%, and more preferably 0.01% to about 0.5% by weight of the suspension.

The pharmaceutical suspensions of the presently disclosed subject matter can be prepared as follows.

(A) admix the thickener with water heated from about 40° C. to about 95° C., preferably from about 40° C. to about 70° C., to form a dispersion if the thickener is not water soluble or a solution if the thickener is water soluble;

(B) admix the sweetening agent with water to form a solution;

(C) admix the flavoring agent with the thickener-water admixture to form a uniform thickener-flavoring agent;

(D) combine the sweetener solution with the thickener-flavoring agent and mix until uniform; and (E) admix the optional adjunct materials such as coloring agents, flavoring agents, decolorants, solubilizers, antifoaming agents, buffers and additional water with the mixture of step (D) to form the suspension.

The flavoring compositions can also be in chewable form. To achieve acceptable stability and quality as well as good taste and mouth feel in a chewable formulation several considerations are important. These considerations include the amount of active substance per tablet, the flavoring agent employed, the degree of compressibility of the tablet and additional properties of the composition.

Chewable pharmaceutical candy is prepared by procedures similar to those used to make soft confectionery. A general discussion of the lozenge and chewable tablet forms of confectionery can be found in H. A. Lieberman and L. Lachman, Pharmaceutical Dosage Forms: Tablets Volume 1, Marcel Dekker, InC, New York, N.Y. (1989) at pages 367 to 418, which disclosure is incorporated herein by reference. In a typical procedure, a boiled sugar-corn syrup blend is formed to which is added a frappe mixture. The boiled sugar-corn syrup blend can be prepared from sugar and corn syrup blended in parts by weight ratio of about 90:10 to about 10:90. The sugar-corn syrup blend is heated to temperatures above about 120° C. to remove water and to form a molten mass. The frappe is generally prepared from gelatin, egg albumin, milk proteins such as casein, and vegetable proteins such as soy protein, and the like, which is added to a gelatin solution and rapidly mixed at ambient temperature to form an aerated sponge like mass. The frappe is then added to the molten candy mass and mixed until homogeneous at temperatures between about 65° C. and about 120° C. The flavor composition can then be added to the homogeneous mixture as the temperature is lowered to about 65° C.-95° C. whereupon additional ingredients can then be added such as flavoring agents and coloring agents. The formulation is further cooled and formed into pieces of desired dimensions.

In other pharmaceutical embodiments, the flavoring agent is incorporated into an ingestible topical vehicle which can be in the form of a mouthwash, rinse, ingestible spray, suspension, dental gel, and the like. Typical non-toxic ingestible vehicles known in the pharmaceutical arts can be used in the presently disclosed subject matter. The preferred ingestible vehicles are water, ethanol, and water-ethanol mixtures. The water-ethanol mixtures are generally employed in a weight ratio from about 1:1 to about 20:1, preferably from about 3:1 to about 20:1, and most preferably from about 3:1 to about 10:1, respectively. The pH value of the ingestible vehicle is generally from about 4 to about 7, and preferably from about 5 to about 6.5. An ingestible topical vehicle having a pH value below about 4 is generally irritating to the ingestible cavity and an ingestible vehicle having a pH value greater than about 7 generally results in an unpleasant mouth feel.

The ingestible topical flavoring agents can also contain conventional additives normally employed in those products. Conventional additives include a fluorine providing compound, a sweetening agent, a flavoring agent, a coloring agent, a humectant, a buffer, and an emulsifier, providing the additives do not interfere with the flavoring properties of the composition. The coloring agents and humectants, and the amounts of these additives to be employed, set out above, can be used in the ingestible topical composition.

The flavoring agents (flavors, flavorants) which can be used include those flavors known to the skilled artisan, such as natural and artificial flavors. Suitable flavoring agents include mints, such as peppermint, citrus flavors such as orange and lemon, artificial vanilla, cinnamon, various fruit flavors, both individual and mixed, and the like.

The amount of flavoring agent employed in the ingestible topical composition is normally a matter of preference subject to such factors as the type of final ingestible composition, the individual flavor employed, and the strength of flavor desired. Thus, the amount of flavoring can be varied in order to obtain the result desired in the final product and such variations are within the capabilities of those skilled in the art without the need for undue experimentation. The flavoring agents, when used, are generally utilized in amounts that can, for example, range in amounts from about 0.05% to about 6%, by weight of the ingestible topical composition.

In accordance with the presently disclosed subject matter, effective amounts of the flavoring agents of the presently disclosed subject matter can be admixed with an ingestible topical vehicle to form a topical composition. These amounts are readily determined by those skilled in the art without the need for undue experimentation. In a preferred embodiment, the ingestible topical flavoring agents will comprise the flavoring agent in an amount from about 0.025% to about 2% and an ingestible topical vehicle in a quantity sufficient to bring the total amount of composition to 100%, by weight of the ingestible topical composition. In a more preferred embodiment, the ingestible topical flavoring agents will comprise the flavoring agent in an amount from about 0.05% to about 1% and an ingestible topical vehicle in a quantity sufficient to bring the total amount of composition to 100%, by weight of the ingestible topical composition.

The presently disclosed subject matter extends to methods for preparing the ingestible topical flavoring agents. In such a method, the ingestible topical composition is prepared by admixing an effective amount of the flavoring agent of the presently disclosed subject matter and an ingestible topical vehicle. The final compositions are readily prepared using standard methods and apparatus generally known by those skilled in the pharmaceutical arts. The apparatus useful in accordance with the presently disclosed subject matter comprises mixing apparatus well known in the pharmaceutical arts, and therefore the selection of the specific apparatus will be apparent to the artisan.

6. Methods of Measuring Taste and Texture Attributes

In certain embodiments of the present application, the taste and texture attributes of a food product can be modified by admixing a flavor composition with the food product as described herein. In certain embodiments, the attribute(s) can be enhanced or reduced by increasing or decreasing the concentration of the flavor composition admixed with the food product. In certain embodiments, the taste or texture attributes of the modified food product can be evaluated as described herein, and the concentration of flavor composition admixed with the food product can be increased or decreased based on the results of the evaluation.

Taste and texture attributes can be reliably and reproducibly measured using sensory analysis methods known as descriptive analysis techniques. The Spectrum™ method of descriptive analysis is described in MORTEN MEILGAARD, D. Sc. ET AL., SENSORY EVALUATION TECHNIQUES (3d ed. 1999). The Spectrum™ method is a custom design approach meaning that the highly trained panelists who generate the data also develop the terminology to measure the attributes of interest. Further, the method uses intensity scales created to capture the intensity differences being investigated. These intensity scales are anchored to a set of well-chosen references. Using these references helps make the data universally understandable and usable over time. This ability to reproduce the results at another time and with another panel makes the data potentially more valuable than analytical techniques which offer similar reproducibility but lack the ability to fully capture the integrated sensory experiences as perceived by humans.

When conducting quantitative descriptive analysis for compounds that modify other compounds, the testing methodology can be adapted to capture the change in character and intensity of the modified compound. For example, when testing for compounds that modify the saltiness of other compounds, the panelists may first taste a salt reference of agreed upon saltiness in order to establish a reference point for comparison. After tasting the reference, panelists may taste and score the test sample for saltiness as well as any other basic taste, chemical feeling factor, or aromatic notes. To quantify any increase in salt perception, the panelists may then taste re-taste the reference and again assign scores for saltiness as well as any other basic taste, chemical feeling factor, or aromatic notes. To quantify any lingering aftertaste, panelists may re-taste the salt reference at 1 minute intervals until their saltiness perception returns to the level of the reference. During the aftertaste evaluations, the panelists also note and score any other basic taste, chemical feeling factor, or aromatic notes.

7. Methods of Synthesis

In certain embodiments, the HMG glucosides of the present application can be synthesized using standard chemosynthesis processes. In certain embodiments, the chemosynthesis process provides an HMG glucoside having a purity of at least 99.999%, or at least 99%, or at least 95%, or at least 90%, or at least 85%, or at least 80%. In certain embodiments, the HMG glucosides can be prepared using standard hydrolysis processes such as those employing acids, enzymes, or a combination of acids and enzymes.

In certain embodiments, the HMG glucoside compositions of the present application comprise one or more compounds of Formula I. Such compounds may, without limitation, be synthesized by any means known in the art. In certain non-limiting embodiments, compounds of Formula I can be synthesized according to the following synthesis scheme:

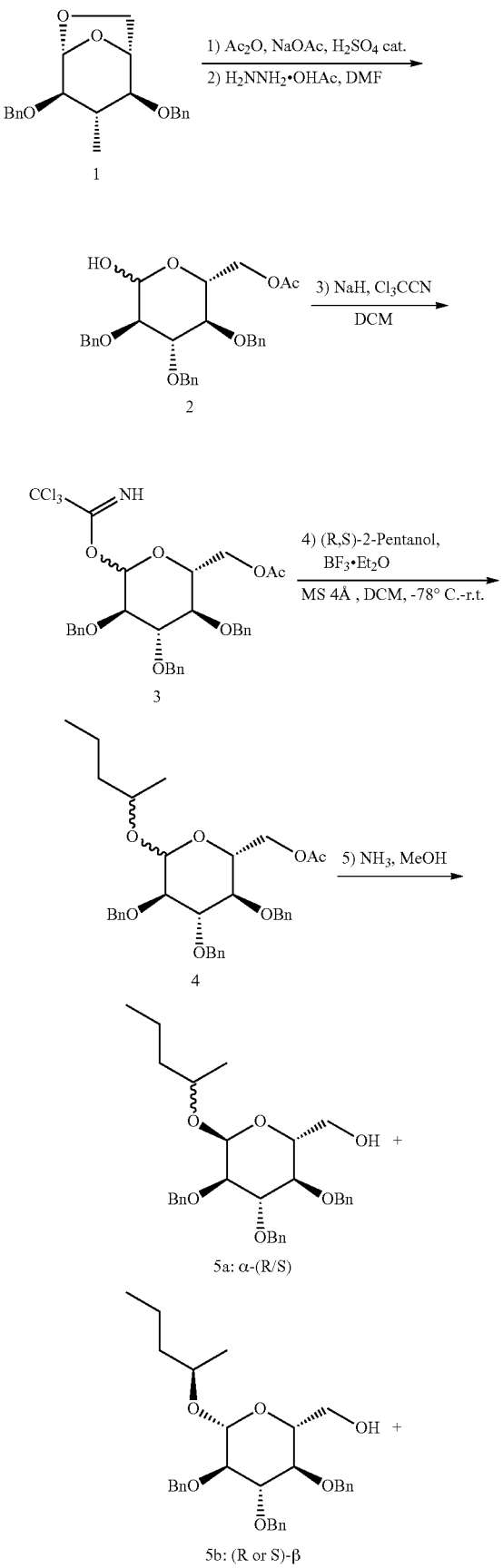

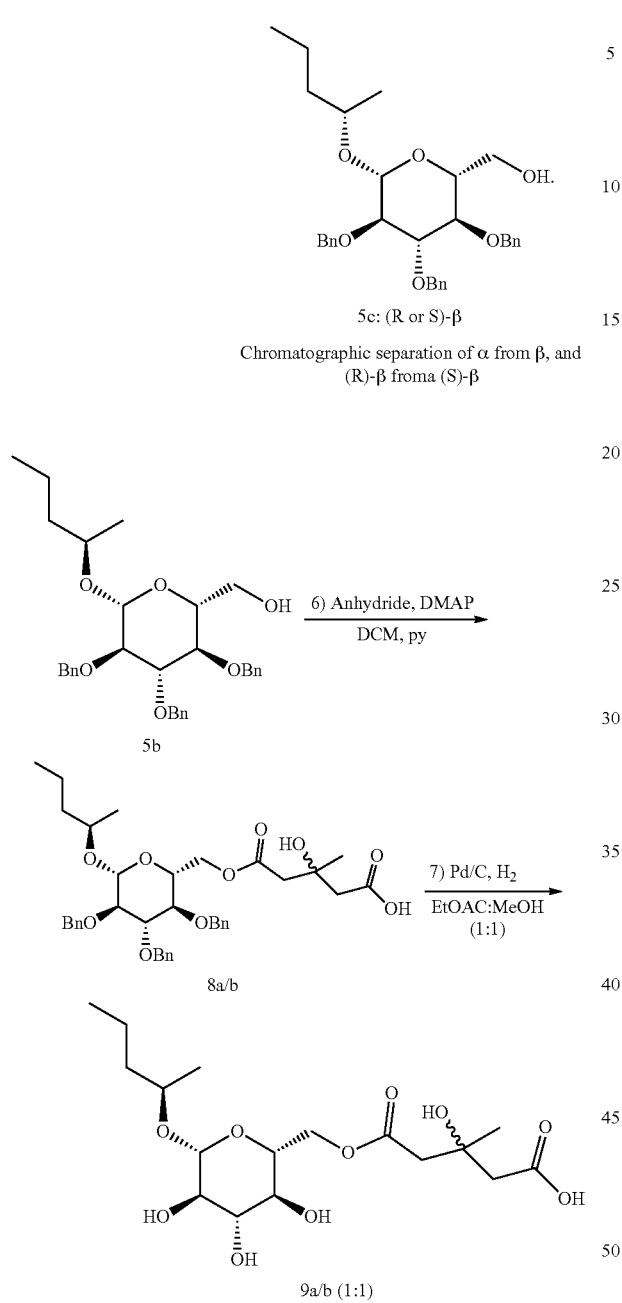
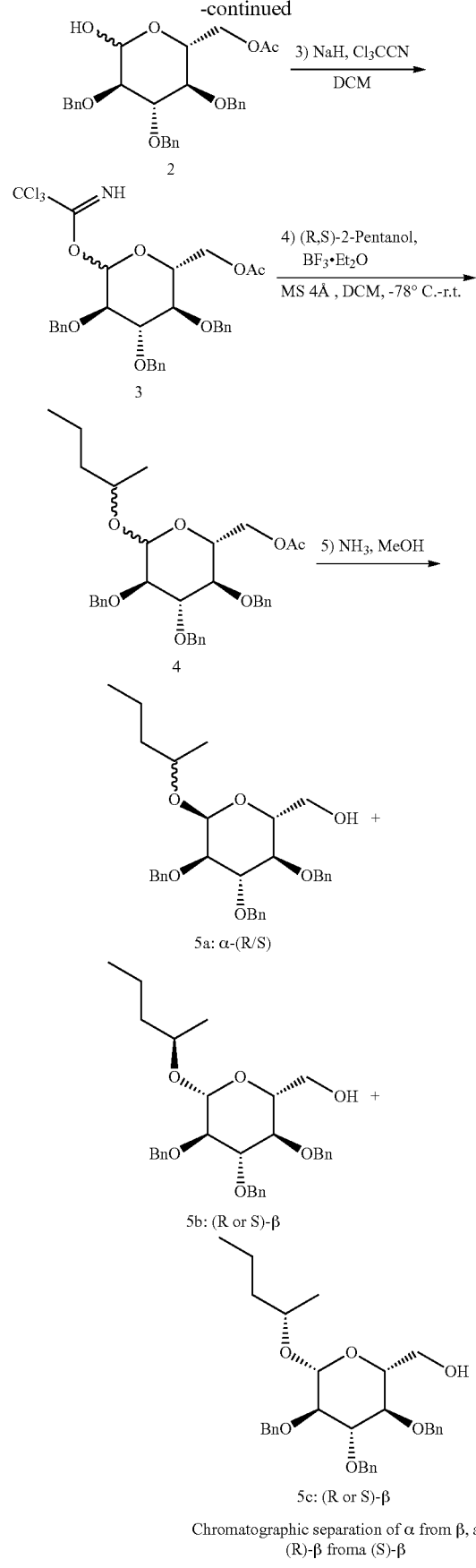
In certain non-limiting embodiments, compounds of Formula I can be synthesized according to the following synthesis scheme:
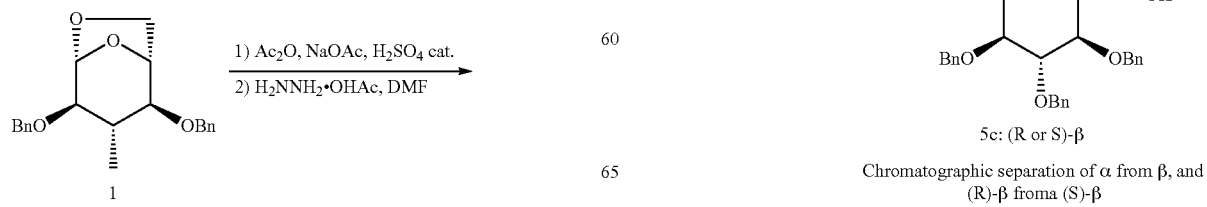

-continued

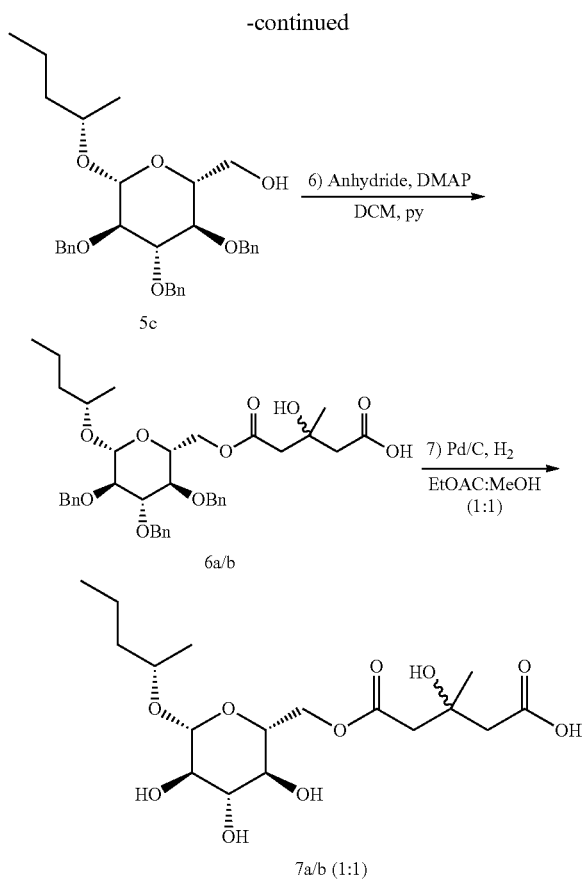

In certain embodiments the HMG glucosides of the present application are prepared from a food product source that is fractionated and/or extracted to form an enriched HMG glucoside composition comprising the HMG glucosides. In certain embodiments, the enriched HMG glucoside composition comprises the flavor composition of the present application and is admixed with a food product according to the methods of the present application. In other embodiments, the enriched HMG glucoside composition is combined with other compositions to form the flavor composition of the present application, which is then admixed with the food product according to the methods of the present application.

In certain embodiments the HMG glucosides of the present application are prepared from a food product source that is hydrolyzed to form a hydrolysate comprising the HMG glucosides. In certain embodiments, the hydrolysate comprises the flavor composition of the present application and is admixed with a food product according to the methods of the present application. In other embodiments, the hydrolysate is combined with other compositions to form the flavor composition of the present application, which is then admixed with the food product according to the methods of the present application.

In certain embodiments the HMG glucosides of the present application are prepared from a food product source that is hydrolyzed and fractionated and/or extracted to form an enriched HMG glucoside hydrolysate composition comprising the HMG glucosides. In certain embodiments, the enriched HMG glucoside hydrolysate composition comprises the flavor composition of the present application and is admixed with a food product according to the methods of the present application. In other embodiments, the enriched HMG glucoside hydrolysate composition is combined with other compositions to form the flavor composition of the present application, which is then admixed with the food product according to the methods of the present application.

EXAMPLES

The presently disclosed subject matter will be better understood by reference to the following Examples, which are provided as exemplary of the invention, and not by way of limitation.

Example 1—Preparation of an HMG Glucoside Composition by Hydrolysis

The present example described the preparation of an HMG glucoside for use in a flavor composition through the hydrolysis of cocoa bean liquor made from West African cocoa beans.

Reagents: A solution of 4N HCl was prepared by adding 100 mL 34-37% HCl in a 250 mL volumetric flask and filling it with water. A solution of 4N NaOH was prepared by dissolving 80 g NaOH pellets in 500 mL of water in a volumetric flask.

Method: Cocoa liquor was run through a sieve and 30.09 g of fine powder was weighed into a 500 mL 3-neck round-bottom flask. The liquor was dissolved in 4N HCl (200 mL) and a stir bar was added to the flask. The sample was stirred at room temperature until the liquor was fully dispersed and flowed freely. A condenser was affixed to the flask and held at 8° C. A digital thermometer was pierced through a rubber stopper to measure the temperature of the solution. The third neck was plugged with a rubber stopper. The flask was wrapped in aluminum foil and heated to approximately 106° C. using a heating mantle. The sample was refluxed for 4.5 hours and left to cool to room temperature. The sample was transferred to a 1 L beaker and neutralized to pH 7 with 4N NaOH using a digital pH meter (pH 6.98 @29° C.). The sample was divided equally into 4 250 mL centrifuge tubes and centrifuged for 10 minutes @ 4500 rpm. The supernatant was filtered under vacuum through a Buchner funnel. The filtrate was then transferred to 2 32 oz plastic containers and lyophilized (yield 52.50 g).

Example 1a—Preparation of an HMG Glucoside Composition by Extraction and Fractionation of a Cocoa Liquor Hydrolysate 1. Hydrolysis of Cocoa Powder
Preparation: A solution of 4N HCl was prepared by adding 100 mL 34-37% HCl in a 250 mL volumetric flask and filling it to the line with water. A solution of 4N NaOH was prepared by dissolving 80 g NaOH pellets in 500 mL of water in a volumetric flask.
Procedure: Cocoa liquor made from *Theobroma cacao* cocoa beans was run through a sieve and 30.09 g of fine powder was weighed into a 500 mL 3-neck round-bottom flask. The liquor was dissolved in 4N HCl (200 mL) and a stir bar was added to the flask. The sample was stirred at room temperature until the liquor was fully dispersed and flowed freely. A condenser was affixed to the flask and held at 8° C. A digital thermometer was pierced through a rubber stopper to measure the temperature of the solution. The third neck was plugged with a rubber stopper. The flask was wrapped in aluminum foil and heated to approximately 106° C. using a heating mantle. The sample was refluxed for 4.5 hours and left to cool to room temperature. The sample was transferred to a 1 L beaker and neutralized to pH 7 with 4N NaOH using a digital pH meter (pH 6.98 @ 29° C.). The sample was divided equally into 4 250 mL centrifuge tubes and centrifuged for 10 minutes @ 4500 rpm. The supernatant was filtered under vacuum through a Buchner funnel. The filtrate was then transferred to 2 32 oz plastic containers and lyophilized.

2. Ethanol Extraction of Hydrolyzed Cocoa Powder

The hydrolyzed cocoa powder was extracted with ethanol to remove a bulk of the salts generated during neutralization. Hydrolyzed cocoa powder (50.36 g) was divided equally into 2 500 mL centrifuge tubes. Ethanol (200 mL) was added slowly to each tube as to not disturb the sample. The samples were shaken for 15 minutes on an autoshaker and then centrifuged for 10 minutes @4500 rpm. The supernatant was decanted into a 1000 mL round-bottom flask. The residue was scraped off the bottom of the tubes and redissolved in ethanol (200 mL each). The samples were shaken for 15 minutes on an autoshaker and then centrifuged for 10 minutes @ 4500 rpm. The supernatant was combined with the previous supernatant and evaporated under reduced pressure to remove all organic solvent. The remaining solids were redissolved in approximately 100 mL deionized water and lyophilized.

3. SPE (Solid Phase Extraction) Fractionation of HCP (Hydrolysed Cocoa Powder) Ethanol Extract The extract previously obtained was further fractionated to exhaustively remove the salts and hydrophilic molecules. HCP ethanol extract was transferred to 14 glass vials (approximately 0.5 g each, 20 mL volume) and dissolved in DI water (10 mL). The samples were shaken until dissolved (approximately 1 minute). The samples were filtered through a syringe and PTFE filter to remove particulates as necessary. A solid phase extraction (SPE) cartridge (20 g/60 mL, C18 stationary phase) was conditioned sequentially with DI water (100 mL), methanol (100 mL), and DI water (100 mL). The sample (10 mL) was then loaded onto cartridge and washed with DI water (100 mL) and extracted with methanol (100 mL). The cartridge was reconditioned and the remaining 13 samples were washed and extracted as previously described. The organic solutions were combined and rotary evaporated under reduced pressure. The residue was redissolved in DI water and lyophilized using a Labconco freeze dryer. The sample was separated by high-performance liquid chromatography (HPLC) to narrow down the taste-active molecules of interest.

Example 1b—Preparation of an HMG Glucoside Composition by Extraction and Fractionation of Cocoa Liquor 1. Liquid/Solid Extraction of Liquor Cocoa Liquor made from cocoa beans sourced from Papua New Guinea (PNG liquor) (600 g) was frozen in liquid nitrogen and ground into a fine powder with a laboratory mill. The powder was divided equally into six plastic centrifuge tubes (500 mL volume). Each sample (100 g PNG liquor) was extracted with diethyl ether (200 mL) for 15 minutes using an autoshaker to remove the fat. After centrifugation (10 min, 4500 rpm), the supernatant was discarded. The extraction process was repeated three more times for a total of four times. The remaining defatted liquor was left to air dry in a fume hood overnight. Defatted liquor (200 g) was divided equally between four plastic centrifuge bottles (250 mL volume). To each sample (50 g defatted PNG liquor), 150 mL 70:30 acetone:water was added. The bottles were placed on an autoshaker for 15 minutes. Each sample was centrifuged (5 min, 3500 rpm) and then the supernatant was vacuum filtered using Whatman 540 filter paper and a Buchner funnel. The residue was freed from the bottom of the bottles by hand and additional 70:30 acetone:water (100 mL) was added to each sample. The samples were shaken for 15 minutes using an auto-shaker. After centrifugation (10 min, 4500 rpm), the supernatant was vacuum filtered again using the same procedure described above. The supernatants from each extraction were combined (~800 mL) and the residue was discarded. The supernatant was rotary evaporated under reduced pressure and the remaining aqueous solution (~250 mL) was transferred into a separatory funnel (1000 mL volume). The aqueous solution was washed with Dichloromethane (3×300 mL) to remove any xanthines. The dichloromethane layer was discarded, then the aqueous solution was washed sequentially with n-butyl acetate (3×300 mL), ethyl acetate (3×300 mL), and methyl acetate (3×300 mL) to remove procyanidins. The organic layers were discarded and the aqueous solution (F7) was rotary evaporated under reduced pressure to remove any remaining solvent. The remaining water solution was lyophilized using a Labconco freeze dryer ($100 \times 10^3$ mbar, −40° C.). Sensory analysis was performed and the savory attribute was found to be in F7.

2. Solid Phase Extraction (SPE)

For removal of any residual salts, treated PNG liquor powder (F7) was transferred to 14 glass vials (20 mL volume, approximately 0.5 g sample in each vial) and dissolved in DI water (10 mL). The samples were shaken until dissolved (approximately 1 minute). A solid phase extraction (SPE) cartridge (20 g/60 mL, C18 stationary phase) was conditioned sequentially with DI water (100 mL), methanol (100 mL), and DI water (100 mL). The vacuum was broken and the sample (10 mL) was then loaded onto cartridge. The vacuum was resumed and the sample was washed with DI water (100 mL). The receptacle flask was changed and the sample was extracted with methanol (100 mL). The cartridge was reconditioned and the remaining 13 samples were washed and extracted as previously described. The organic solutions were combined and rotary evaporated under reduced pressure. The residue was redissolved in DI water and lyophilized using a Labconco freeze dryer ($100 \times 10^3$ mbar, −40° C.). Sensory analysis confirmed the presence of the savory attribute in the organic fraction.

Example 2—Preparation of an HMG Glucoside Composition by Synthetic Chemosynthesis HMG glucosides described by the present application were prepared through synthetic chemosynthesis methods described in synthesis schemes 1 and 2 below.

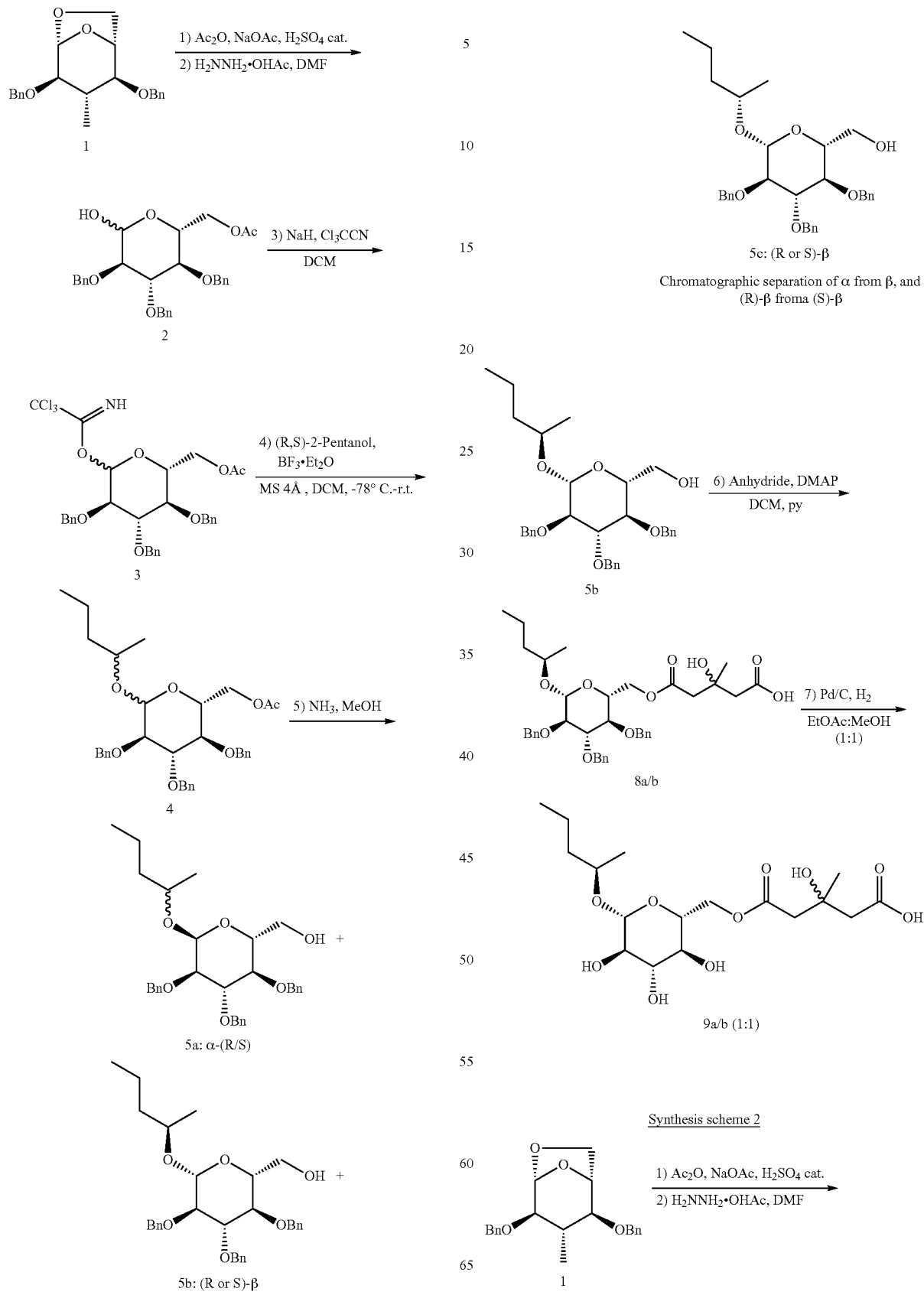

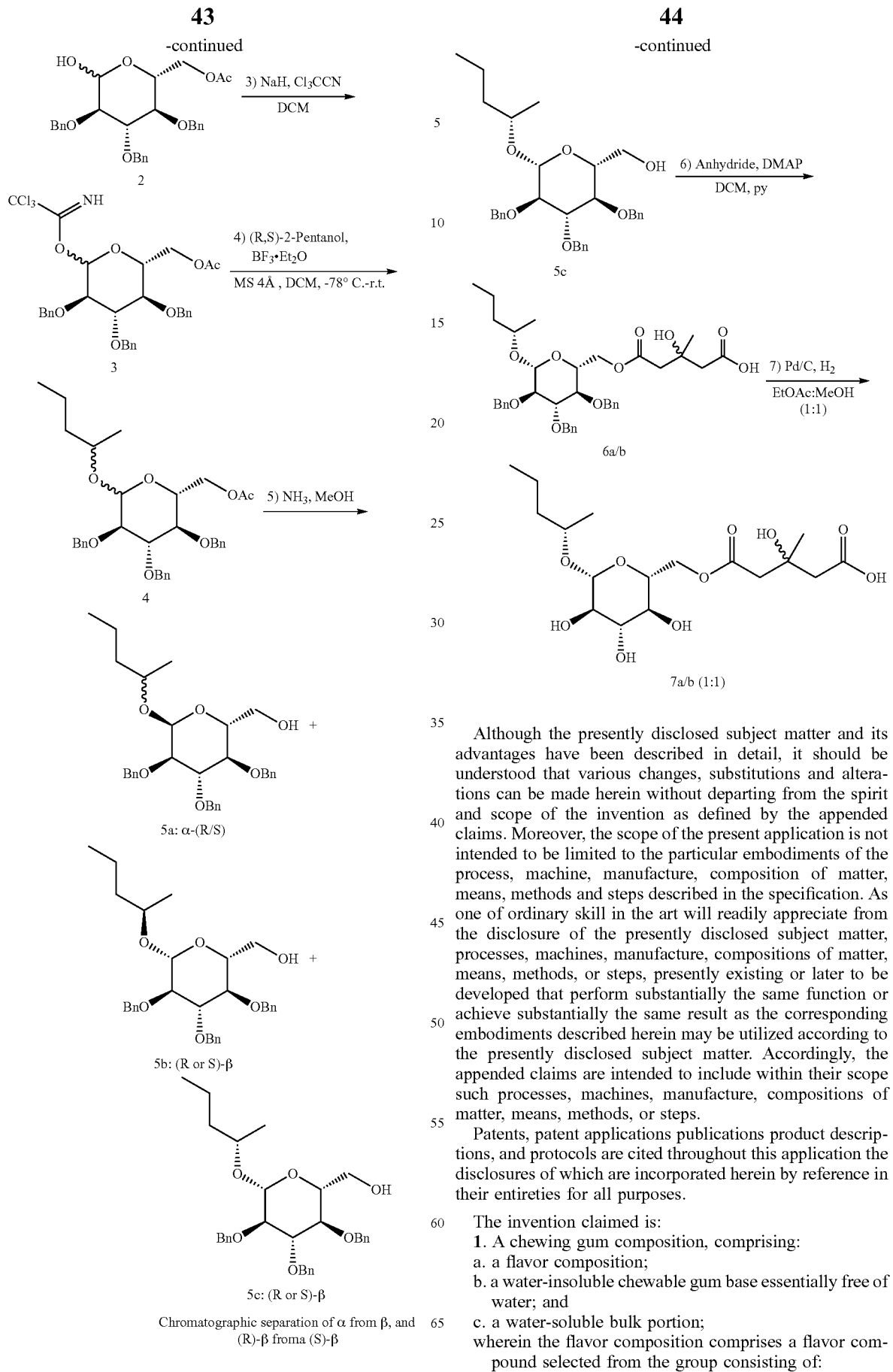

Although the presently disclosed subject matter and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein may be utilized according to the presently disclosed subject matter. Accordingly, the appended claims are intended to include within their scope such processes, machines, manufacture, compositions of matter, means, methods, or steps.

Patents, patent applications publications product descriptions, and protocols are cited throughout this application the disclosures of which are incorporated herein by reference in their entireties for all purposes.

The invention claimed is:
1. A chewing gum composition, comprising:
 a. a flavor composition;
 b. a water-insoluble chewable gum base essentially free of water; and
 c. a water-soluble bulk portion;
 wherein the flavor composition comprises a flavor compound selected from the group consisting of:

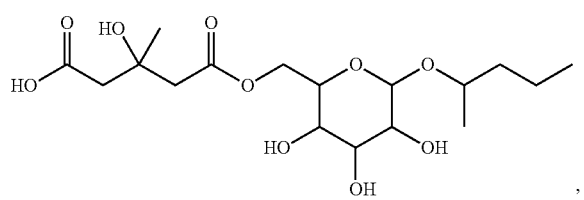

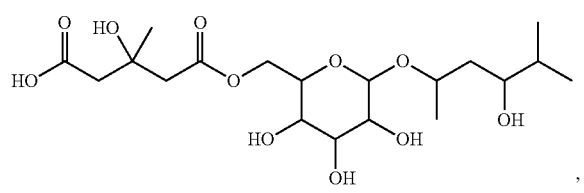

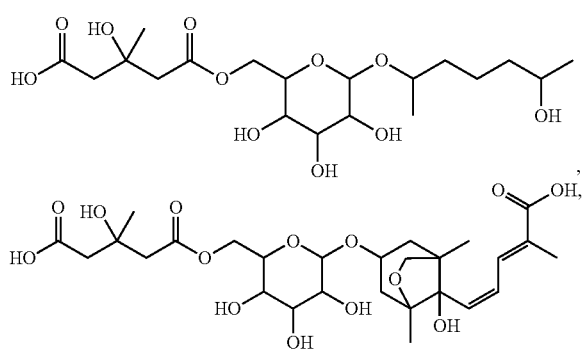

and combinations thereof.

2. The chewing gum composition of claim 1, wherein the flavor compound is:

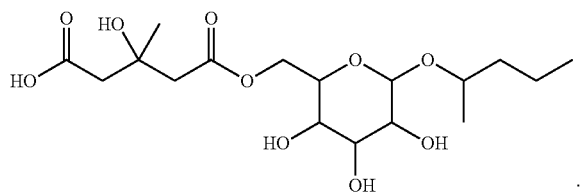 [SMILES: CCCC(C)OC1OC(COC(=O)CC(C)(O)CC(=O)O)C(O)C(O)C1O]

3. The chewing gum composition of claim 1, wherein the flavor compound is selected from the group consisting of:

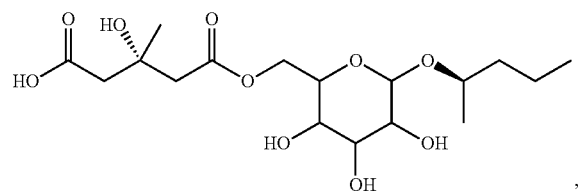

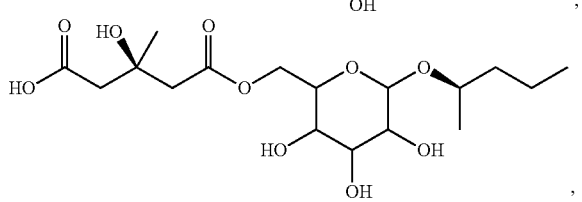

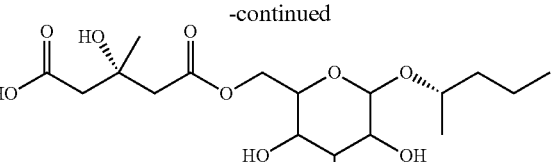

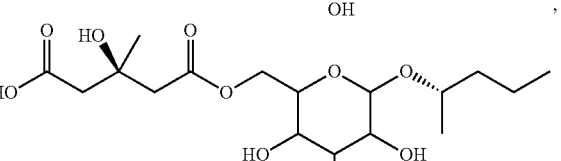

and combinations thereof.

4. The chewing gum composition of claim 1, wherein the flavor compound is added at a concentration of from about 0.0000001% to about 1.0% in the chewable gum composition.

5. The chewing gum composition of claim 1, wherein the flavor composition is admixed with the chewing gum composition in an amount effective to increase or decrease mouthfeels selected from the group consisting of a savory mouthfeel, a mouth-watering mouthfeel, a lubricating mouthfeel, a slippery mouthfeel, an astringent mouthfeel, and combinations thereof.

6. The chewing gum composition of claim 1, wherein the gum base comprises an additional component selected from the group consisting of elastomers, elastomer solvents, plasticizers, waxes, emulsifiers, inorganic fillers, plastic polymers, and combinations thereof.

7. The chewing gum composition of claim 1, wherein the gum base constitutes between about 5% to about 95% by weight of the gum composition.

8. The chewing gum composition of claim 1, wherein the gum base further comprises a filler component selected from the group consisting of calcium carbonate, magnesium carbonate, talc, dicalcium phosphate, and combinations thereof.

9. The chewing gum composition of claim 1, wherein the gum base further comprises a softener selected from the group consisting of glycerol monostearate, glycerol triacetate, and combinations thereof.

10. The chewing gum composition of claim 1, wherein the gum base further comprises a component selected from the group consisting of antioxidants, colors, emulsifiers, and combinations thereof.

11. The chewing gum composition of claim 1, wherein the water-soluble portion further comprises a component selected from the group consisting of softeners, sweeteners, flavors, physiological cooling agents, and combinations thereof.

12. The chewing gum composition of claim 1, wherein the flavor composition is at a concentration of from about 0.1 to about 5,000 ppm of the chewing gum composition.

13. The chewing gum composition of claim 1, wherein the gum composition is a sugarless gum composition.

14. The chewing gum composition of claim 11, wherein the sweetener is a sugar sweetener selected from the group consisting of sucrose, dextrose, maltose, dextrin, dried invert sugar, fructose, galactose, corn syrup solids, and the combinations thereof.

15. The chewing gum composition of claim 11, wherein the sweetener is a sugarless sweetener selected from the group consisting of sorbitol, hydrogenated isomaltulose, mannitol, xylitol, lactitol, erythritol, hydrogenated starch hydrolysate, maltitol, and the combinations thereof.

* * * * *